(12) United States Patent
Van Gompel et al.

(10) Patent No.: US 7,785,309 B2
(45) Date of Patent: Aug. 31, 2010

(54) DISPOSABLE GARMENT WITH BIAXIALLY STRETCHABLE INNER LAYER

(75) Inventors: Paul Theodore Van Gompel, Hortonville, WI (US); Gary Alan Krueger, Neenah, WI (US); Lu Ann Marie Beckman, Neenah, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 588 days.

(21) Appl. No.: 11/215,978

(22) Filed: Aug. 31, 2005

(65) Prior Publication Data

US 2007/0049895 A1 Mar. 1, 2007

(51) Int. Cl.
*A61F 13/15* (2006.01)
*A61F 13/20* (2006.01)

(52) U.S. Cl. .................. 604/385.101; 604/385.01; 604/385.24

(58) Field of Classification Search ............ 604/385.01, 604/385.22–385.3
See application file for complete search history.

(56) References Cited

U.S. PATENT DOCUMENTS

| | | | |
|---|---|---|---|
| 3,699,966 A | 10/1972 | Chapuis |
| 3,744,494 A | 7/1973 | Marsan |
| 3,863,637 A | 2/1975 | MacDonald et al. |
| 3,920,017 A | 11/1975 | Karami |
| 3,930,501 A | 1/1976 | Schaar |
| 3,951,150 A | 4/1976 | Schaar |
| 3,978,861 A | 9/1976 | Schaar |
| 3,987,794 A | 10/1976 | Schaar |
| 3,990,450 A | 11/1976 | Schaar |
| 3,995,640 A | 12/1976 | Schaar |
| 4,022,456 A | 5/1977 | Hooper et al. |
| 4,040,423 A | 8/1977 | Jones, Sr. |
| 4,041,950 A | 8/1977 | Jones, Sr. |
| 4,081,301 A | 3/1978 | Buell |
| 4,205,679 A | 6/1980 | Repke et al. |
| 4,488,927 A | 12/1984 | Hooper |
| 4,543,154 A | 9/1985 | Reiter |
| 4,610,679 A | 9/1986 | Matsushita |

(Continued)

FOREIGN PATENT DOCUMENTS

EP 1201212 A2 5/2002

(Continued)

OTHER PUBLICATIONS

International Search Report for PCT/US2006/021458 dated Nov. 21, 2006, 4 pages.

*Primary Examiner*—Michele Kidwell
(74) *Attorney, Agent, or Firm*—Armstrong Teasdale, LLP

(57) ABSTRACT

A disposable absorbent garment having an inner layer with a first end panel, a second end panel, and a pair of side panels formed separate from the first and second end panels. The first and second end panels are stretchable in at least the lateral direction of the garment. The side panels extend longitudinally between the first and second end panels in laterally spaced relationship with each other such that the end panels and side panels together define a central opening of the inner layer. The side panels are each secured to the first and second end panels and are extensible in at least the lateral direction of the garment. The garment includes an outer layer is in opposed relationship with the inner layer and an absorbent assembly disposed between the inner layer and the outer layer.

26 Claims, 7 Drawing Sheets

U.S. PATENT DOCUMENTS

| | | | |
|---|---|---|---|
| 4,657,802 A | 4/1987 | Morman | |
| 4,662,877 A | 5/1987 | Williams | |
| 4,663,220 A | 5/1987 | Wisneski et al. | |
| 4,681,580 A | 7/1987 | Reising et al. | |
| 4,738,677 A | 4/1988 | Foreman | |
| 4,743,246 A | 5/1988 | Lawson | |
| 4,753,646 A | 6/1988 | Enloe | |
| 4,795,454 A | 1/1989 | Dragoo | |
| 4,798,603 A | 1/1989 | Meyer et al. | |
| 4,808,177 A | 2/1989 | DesMarais et al. | |
| 4,816,025 A | 3/1989 | Foreman | |
| 4,822,668 A | 4/1989 | Tanaka et al. | |
| 4,865,596 A | 9/1989 | Weisman et al. | |
| 4,879,170 A | 11/1989 | Radwanski et al. | |
| 4,883,481 A | 11/1989 | Blanchard | |
| 4,938,754 A | 7/1990 | Mesek | |
| 4,938,755 A | 7/1990 | Foreman | |
| 4,965,122 A | 10/1990 | Morman | |
| 4,990,147 A * | 2/1991 | Freeland | 604/385.22 |
| 5,026,364 A | 6/1991 | Robertson | |
| 5,085,654 A | 2/1992 | Buell | |
| 5,087,255 A | 2/1992 | Sims | |
| 5,114,781 A | 5/1992 | Morman | |
| 5,176,668 A | 1/1993 | Bernardin | |
| 5,176,672 A | 1/1993 | Bruemmer et al. | |
| 5,190,606 A | 3/1993 | Merkatoris et al. | |
| 5,192,606 A | 3/1993 | Proxmire et al. | |
| 5,226,992 A | 7/1993 | Morman | |
| 5,254,111 A | 10/1993 | Cancio et al. | |
| 5,263,949 A | 11/1993 | Karami et al. | |
| 5,269,775 A * | 12/1993 | Freeland et al. | 604/385.22 |
| 5,304,159 A | 4/1994 | Tanji et al. | |
| 5,304,160 A | 4/1994 | Igaue et al. | |
| 5,330,598 A | 7/1994 | Erdman et al. | |
| 5,380,310 A | 1/1995 | Mitrani | |
| 5,383,988 A | 1/1995 | Herrmann et al. | |
| 5,397,318 A | 3/1995 | Dreier | |
| 5,429,632 A | 7/1995 | Tanji et al. | |
| 5,451,219 A | 9/1995 | Suzuki et al. | |
| 5,509,915 A | 4/1996 | Hanson et al. | |
| 5,531,730 A | 7/1996 | Dreier | |
| 5,540,671 A | 7/1996 | Dreier | |
| 5,558,660 A | 9/1996 | Dreier | |
| 5,558,661 A | 9/1996 | Roe et al. | |
| 5,582,606 A | 12/1996 | Bruemmer et al. | |
| 5,584,828 A | 12/1996 | Yamamoto et al. | |
| 5,593,401 A | 1/1997 | Sosalla et al. | |
| 5,595,618 A | 1/1997 | Fries et al. | |
| 5,599,417 A | 2/1997 | Glaug et al. | |
| 5,601,543 A | 2/1997 | Glaug et al. | |
| 5,645,542 A | 7/1997 | Anjur et al. | |
| 5,649,918 A | 7/1997 | Schleinz | |
| 5,674,213 A | 10/1997 | Sauer | |
| 5,683,531 A | 11/1997 | Roessler et al. | |
| 5,695,488 A * | 12/1997 | Sosalla | 604/385.24 |
| 5,695,868 A | 12/1997 | McCormack | |
| 5,716,478 A | 2/1998 | Boothe et al. | |
| 5,752,947 A | 5/1998 | Awolin | |
| 5,810,800 A | 9/1998 | Hunter et al. | |
| 5,827,259 A | 10/1998 | Laux et al. | |
| 5,833,677 A | 11/1998 | Sauer | |
| 5,843,056 A | 12/1998 | Good et al. | |
| 5,851,204 A | 12/1998 | Mizutani | |
| 5,855,999 A | 1/1999 | McCormack | |
| 5,865,825 A | 2/1999 | Schlinz | |
| 5,876,390 A | 3/1999 | Hall et al. | |
| 5,879,341 A | 3/1999 | Odorzynski et al. | |
| 5,895,382 A | 4/1999 | Popp et al. | |
| 5,904,675 A | 5/1999 | Laux et al. | |
| 5,919,179 A | 7/1999 | Faulks et al. | |
| 5,931,826 A | 8/1999 | Faulks et al. | |
| 5,938,652 A | 8/1999 | Sauer | |
| 5,947,947 A | 9/1999 | Tanzer et al. | |
| 5,947,948 A | 9/1999 | Roe et al. | |
| 5,964,743 A | 10/1999 | Abuto et al. | |
| 5,993,433 A | 11/1999 | St. Louis et al. | |
| 6,120,486 A | 9/2000 | Toyoda et al. | |
| 6,121,510 A | 9/2000 | Sauer | |
| 6,132,410 A | 10/2000 | Van Gompel et al. | |
| 6,142,985 A | 11/2000 | Feist | |
| 6,183,459 B1 | 2/2001 | Yamamoto et al. | |
| 6,193,701 B1 | 2/2001 | Van Gompel et al. | |
| 6,217,563 B1 | 4/2001 | Van Gompel et al. | |
| 6,221,062 B1 | 4/2001 | Osborn, III | |
| 6,231,557 B1 | 5/2001 | Krautkramer et al. | |
| 6,248,097 B1 | 6/2001 | Beitz et al. | |
| 6,258,076 B1 | 7/2001 | Glaug et al. | |
| 6,262,331 B1 | 7/2001 | Nakahata et al. | |
| 6,264,639 B1 | 7/2001 | Sauer | |
| 6,264,641 B1 | 7/2001 | Van Gompel et al. | |
| 6,280,426 B1 | 8/2001 | Turner et al. | |
| 6,287,169 B1 | 9/2001 | Willms et al. | |
| 6,325,787 B1 | 12/2001 | Roe et al. | |
| 6,362,389 B1 | 3/2002 | McDowall et al. | |
| 6,450,996 B1 | 9/2002 | Otsubo | |
| 6,482,191 B1 | 11/2002 | Roe et al. | |
| 6,491,677 B1 | 12/2002 | Glaug et al. | |
| 6,503,236 B1 | 1/2003 | Uitenbroek et al. | |
| 6,506,185 B1 | 1/2003 | Sauer | |
| 6,506,186 B1 | 1/2003 | Roessler et al. | |
| 6,552,245 B1 | 4/2003 | Roessler et al. | |
| 6,562,015 B1 | 5/2003 | Wilson | |
| 6,570,056 B1 | 5/2003 | Tanzer et al. | |
| 6,572,598 B1 | 6/2003 | Ashton et al. | |
| 6,582,413 B2 | 6/2003 | Krautkramer et al. | |
| 6,602,234 B2 | 8/2003 | Klemp et al. | |
| 6,605,552 B2 | 8/2003 | Jackson et al. | |
| 6,610,900 B1 | 8/2003 | Tanzer | |
| 6,627,564 B1 | 9/2003 | Morman et al. | |
| 6,638,260 B2 | 10/2003 | Mishima | |
| 6,680,423 B1 | 1/2004 | Tanzer | |
| 6,682,512 B2 | 1/2004 | Uitenbroek et al. | |
| 6,685,690 B2 | 2/2004 | Ikeda et al. | |
| 6,706,030 B1 | 3/2004 | Okuda et al. | |
| 6,753,455 B2 | 6/2004 | Chmielewski | |
| 6,773,810 B2 | 8/2004 | Sen et al. | |
| 6,790,202 B2 | 9/2004 | Klemp et al. | |
| 6,846,448 B2 | 1/2005 | Rymer et al. | |
| 6,851,593 B2 | 2/2005 | Weber et al. | |
| 6,869,423 B2 | 3/2005 | Onishi et al. | |
| 6,881,205 B2 | 4/2005 | Zehner et al. | |
| 6,890,327 B2 | 5/2005 | Suzuki et al. | |
| 6,921,394 B2 | 7/2005 | Sayama et al. | |
| 7,008,497 B2 | 3/2006 | Nakakado et al. | |
| 7,166,094 B2 | 1/2007 | Glaug et al. | |
| 7,220,478 B2 | 5/2007 | McCormack et al. | |
| 2001/0025165 A1 | 9/2001 | Shimoe | |
| 2002/0052591 A1 | 5/2002 | Zehner et al. | |
| 2003/0050616 A1 | 3/2003 | Reynolds et al. | |
| 2003/0114817 A1 | 6/2003 | Roessler et al. | |
| 2003/0114819 A1 | 6/2003 | Sayama et al. | |
| 2003/0119400 A1 | 6/2003 | Beitz et al. | |
| 2003/0125695 A1 | 7/2003 | Dorschner | |
| 2003/0125696 A1 | 7/2003 | Morman et al. | |
| 2003/0208171 A1 | 11/2003 | Zehner et al. | |
| 2004/0044323 A1 | 3/2004 | Roessler et al. | |
| 2004/0116888 A1 | 6/2004 | Dorschner | |
| 2004/0127878 A1 | 7/2004 | Olson et al. | |
| 2004/0127882 A1 | 7/2004 | Weber | |
| 2004/0133182 A1 | 7/2004 | Mishima | |
| 2004/0204698 A1 | 10/2004 | Zenker et al. | |
| 2005/0043460 A1 | 2/2005 | McCormack et al. | |
| 2005/0074584 A1 | 4/2005 | Zehner et al. | |
| 2005/0095942 A1 | 5/2005 | Mueller et al. | |

| | | | | | |
|---|---|---|---|---|---|
| 2005/0101206 A1 | 5/2005 | McCormack et al. | 2008/0147025 A1 | 6/2008 | Van Gompel et al. |
| 2005/0131377 A1 | 6/2005 | Franke et al. | | | |
| 2005/0133151 A1 | 6/2005 | Maldonado Pacheco et al. | | | |

FOREIGN PATENT DOCUMENTS

| | | | |
|---|---|---|---|
| 2005/0143710 A1 | 6/2005 | Van Gompel et al. | |
| 2005/0148987 A1 | 7/2005 | Van Gompel et al. | EP 1214921 A1 6/2002 |
| 2006/0247599 A1 | 11/2006 | Mullen et al. | WO WO 02/34184 5/2002 |
| 2007/0049895 A1 | 3/2007 | Van Gompel et al. | |
| 2008/0141839 A1 | 6/2008 | Van Gompel et al. | * cited by examiner |

DISPOSABLE GARMENT WITH BIAXIALLY STRETCHABLE INNER LAYER

BACKGROUND OF THE INVENTION

This invention relates generally to a disposable garment for personal wear, and more particularly to such a disposable garment with improved fit and reduced leakage.

Disposable garments are known for use in the manner of underpants for children and adults, garments worn like training pants for toddlers and garments worn like diapers for infants. Disposable absorbent garments are designed to absorb and contain bodily fluids but otherwise have a limited period of use before its ability to perform its intended function is exhausted. In particular, such disposable absorbent garments are intended to be discarded after one or more insults instead of being laundered.

Typically, it is desirable for disposable garments to fit close to the body of the wearer for comfort and discretion. Presently available disposable garments for wear about one's waist include a substantially liquid impermeable outer cover, a liquid permeable bodyside liner in a superposed relation with the outer cover, and an absorbent structure located between the outer cover and the bodyside liner for taking in and retaining liquid body exudates. The side edges of the garment form a pair of leg openings when the disposable garment is worn and the ends of the garment together form the waist opening thereof. Elastic components such as waist elastics, leg elastics and containment flaps are commonly used to enhance the fit and inhibit leakage from the garment.

While disposable garments have been known for many years, the materials used to construct them have continuously evolved as a result of new technologies for formulating and manufacturing disposable materials. Materials may be selected for performance or to provide a cost advantage, particularly given that many manufacturers produce disposable garments and disposable absorbent garments in very large quantities. One aspect of evolution has been the development and availability of stretchable materials to replace previously non-stretchable components in order to provide improvements in the way in which the garments fit and improvements in the range of fit of the garments.

With the advent of the availability of stretchable materials to construct disposable absorbent garments, various configurations for garments incorporating stretchable materials have been described. For example, once a stretchable material is selected to form a component of a garment, the material may be modified to provide a range of stretch characteristics. U.S. Pat. No. 6,193,701 (hereinafter "the '701 patent") describes personal care articles that may include resiliently stretchable outer covers and/or resiliently stretchable bodyside liners.

In addition to garments utilizing extensible and otherwise stretchable materials, garments utilizing elastic materials have been described. International Publication No. WO 02/34184 (hereinafter "the 34184 publication") describes absorbent garments that may have a biaxially stretchable outer cover and a biaxially stretchable bodyside liner. The "biaxially stretchable" materials described as being suitable in the 34184 publication include elastic materials capable of stretching in at least two directions.

Simultaneous with the development of stretchable materials having lower cost and/or improved properties for use in disposable garments, developments with regard to the structural features of disposable garments have also occurred. An example of one such class of features is the provision of holes or apertures between layers of the garments to separate the waste materials from the wearer's skin. More specific examples of such features are apertures or openings in the bodyside liners of disposable absorbent garments that are provided to separate solid wastes from the wearer's skin to reduce the incidence of troublesome conditions such as diaper rash.

Even though significant and numerous advancements have occurred in the materials and structural features available for the construction of disposable garments, there remain opportunities for improvement in the fit and containment capacity of such garments. For example, there remains a need for a disposable garment that provides improved fit on the wearer while inhibiting leakage and keeping the waste materials contained by the garment away from the skin of the wearer.

SUMMARY OF THE INVENTION

In one embodiment, a disposable absorbent garment generally has a longitudinal direction, a lateral direction, a front waist region, a back waist region and a crotch region extending longitudinally between and interconnecting the front waist region and the back waist region, longitudinal ends and lateral side edges. The disposable absorbent garment generally comprises an inner layer having an interior surface for facing a wearer of the garment and an exterior surface. The inner layer has a first end panel at least in part defining the front waist region of the garment, a second end panel separate from the first end panel and longitudinally spaced therefrom to at least in part define the back waist region of the garment, the first and second end panels each being stretchable in at least the lateral direction of the garment, and a pair of side panels formed separate from the first and second end panels. The side panels extend longitudinally between the first and second end panels in laterally spaced relationship with each other such that the end panels and side panels together define a central opening of the inner layer. The side panels each being secured to the first and second end panels and being extensible in at least the lateral direction of the garment. The garment includes an outer layer in opposed relationship with the inner layer and an absorbent assembly disposed between the inner layer and the outer layer for receiving body waste that passes through the inner layer at the central opening. The absorbent assembly being secured to the inner layer and being sized larger than the central opening of the inner layer for underlying substantially the entire opening.

In another embodiment, a disposable absorbent garment generally has a longitudinal direction, a lateral direction, a front waist region, a back waist region and a crotch region extending longitudinally between and interconnecting the front waist region and the back waist region, longitudinal ends and lateral side edges. The disposable absorbent garment generally comprises an inner layer having an interior surface for facing a wearer of the garment and an exterior surface. The inner layer has a first end panel at least in part defining the front waist region of the garment, a second end panel separate from the first end panel and longitudinally spaced from the first end panel to at least in part define the back waist region of the garment, the first and second end panels each being stretchable in at least the lateral direction of the garment, and a pair of laterally spaced side panels extending longitudinally between and secured to the first and second end panels to at least in part define the crotch region of the garment. The side panels are extensible in at least the lateral direction of the garment. The end panels and the side panels together defining a central opening of the inner layer. The garment includes an outer layer in opposed relationship with the inner layer and an absorbent assembly disposed between the inner layer and the outer layer for receiving body waste that passes through the inner layer. The absorbent assembly has laterally spaced edge margins, each edge margin of the absorbent assembly being secured to a respective one of the side panels along a respective longitudinal line of attachment whereby at least a longitudinal segment of each side panel is positionable about the line of attachment and relative to and independent of the absorbent assembly and end panels. Each side panel includes a longitudinally extending elastic member extending along at least the longitudinal segment of the side panel. The elastic member is in laterally spaced relationship with the longitudinal line of attachment between the absorbent assembly edge margin and the respective side panel to generally urge the longitudinal segment of the side panel against the wearer.

In another embodiment, a disposable absorbent garment for personal wear generally has a longitudinal direction and a lateral direction. The disposable absorbent garment generally comprises an inner layer having an interior surface for facing a wearer of the garment, and an exterior surface. The inner layer has a first end panel and a second end panel spaced longitudinally from the first end panel, the first and second end panels each being stretchable in at least the lateral direction of the garment, and a pair of laterally spaced side panels extending longitudinally between and secured to the first and second end panels. The side panels and end panels together define a central opening of the inner layer. At least a portion of each of the side panels defines leg cuffs of the garment adapted for contact with the wearer's legs. The leg cuff portion of each side panel is extensible in at least the lateral direction of the garment and comprises at least one longitudinally extending elastic member for urging the leg cuff generally against the garment wearer's skin. The disposable absorbent garment includes an outer layer in opposed relationship with the inner layer and an absorbent assembly disposed between the inner layer and the outer layer for receiving body waste that passes through the inner layer. The absorbent assembly having laterally spaced edge margins. Each edge margin of the absorbent assembly is secured to a respective one of the side panels along a respective longitudinal line of attachment disposed laterally inward of the leg cuff portion of the side panel such that the at least one elastic member of the leg cuff is disposed laterally outboard of the longitudinal line of the attachment. The leg cuff portion of each side panel is free from securement to the absorbent assembly and the end panels of the garment at least along a longitudinal segment of each leg cuff portion so that the leg cuff portion along the segment is stretchable in the lateral direction of the garment independent of the absorbent assembly and the end panels.

In yet another embodiment, a disposable absorbent garment generally has a longitudinal direction, a lateral direction, a front waist region, a back waist region and a crotch region extending longitudinally between and interconnecting the front waist region and the back waist region, longitudinal ends and lateral side edges. The disposable absorbent garment generally comprises an inner layer having an interior surface for facing a wearer of the garment, and an exterior surface, the inner layer having a first end panel at least in part defining the front waist region of the garment, a second end panel separate from the first end panel and longitudinally spaced from the first end panel to at least in part define the back waist region of the garment, the first and second end panels each being stretchable in at least the lateral direction of the garment, and a pair of laterally spaced side panels formed separate from the first and second end panels and extending longitudinally between and secured to the first and second end panels to at least in part define the crotch region of the garment. The side panels each have an inboard edge and an outboard edge and are elastic in at least the longitudinal direction of the garment. The end panels and side panels together defining a central opening of the inner layer. The disposable absorbent garment includes an outer layer in opposed relationship with the inner layer and an absorbent assembly disposed between the inner layer and the outer layer for receiving body waste that passes through the inner layer. The absorbent assembly has laterally spaced edge margins, each edge margin of the absorbent assembly being secured to a respective one of the side panels along a respective longitudinal line of attachment disposed laterally between the inboard and outboard edges of the side panel. The inboard and outboard edges of each side panel are positionable about the respective line of attachment relative to and independent of the absorbent assembly and the end panels along at least a longitudinal segment of each side panel.

BRIEF DESCRIPTION OF THE DRAWINGS

Corresponding reference characters indicate corresponding parts throughout the several views of the drawings.

DETAILED DESCRIPTION OF THE INVENTION

Figure 1:
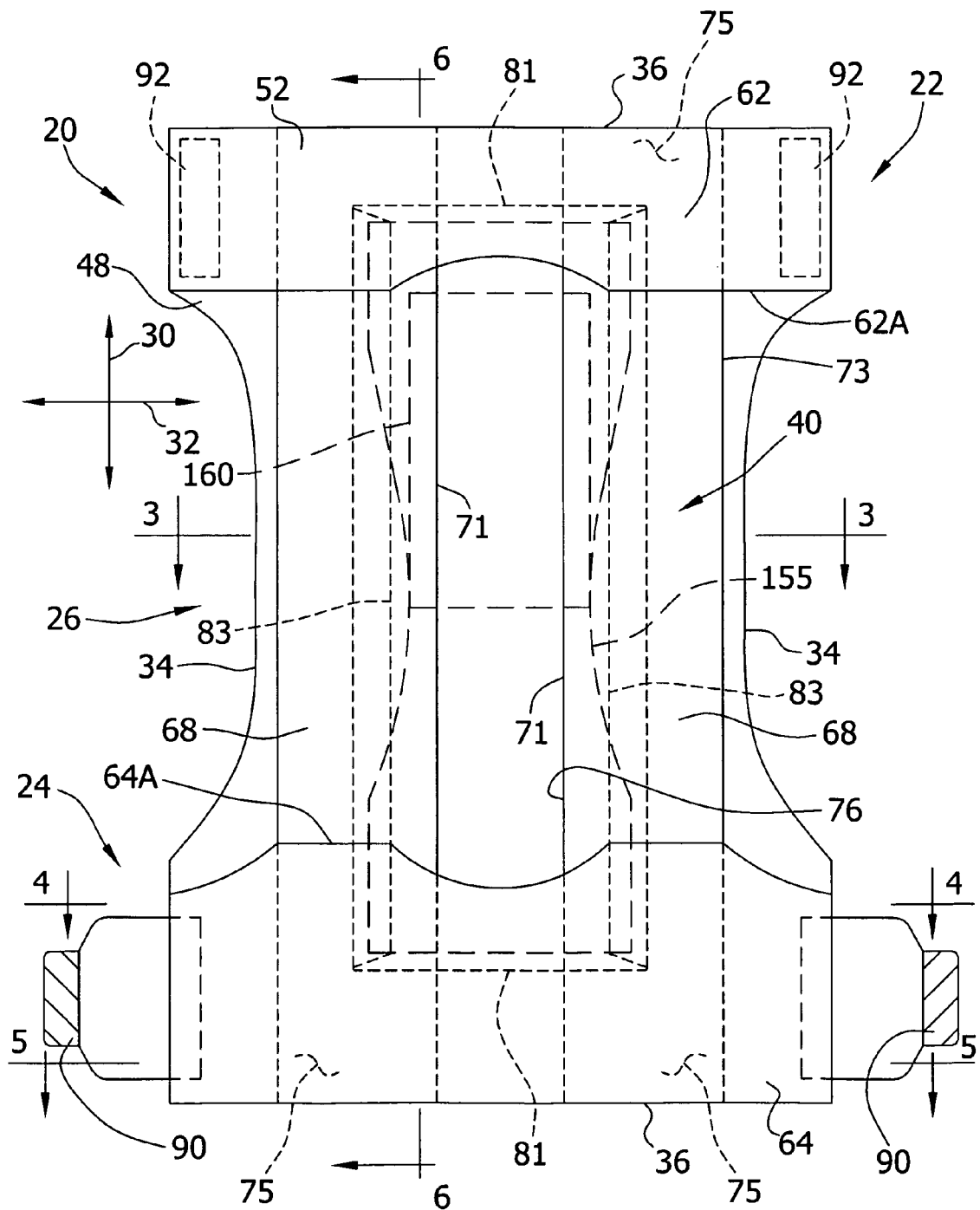
FIG. 1 is a top plan view of a disposable garment of the present invention in the form of a diaper illustrated in an unfolded and laid flat condition to show the surface of the diaper that contacts the skin of the wearer.
Figure 2:
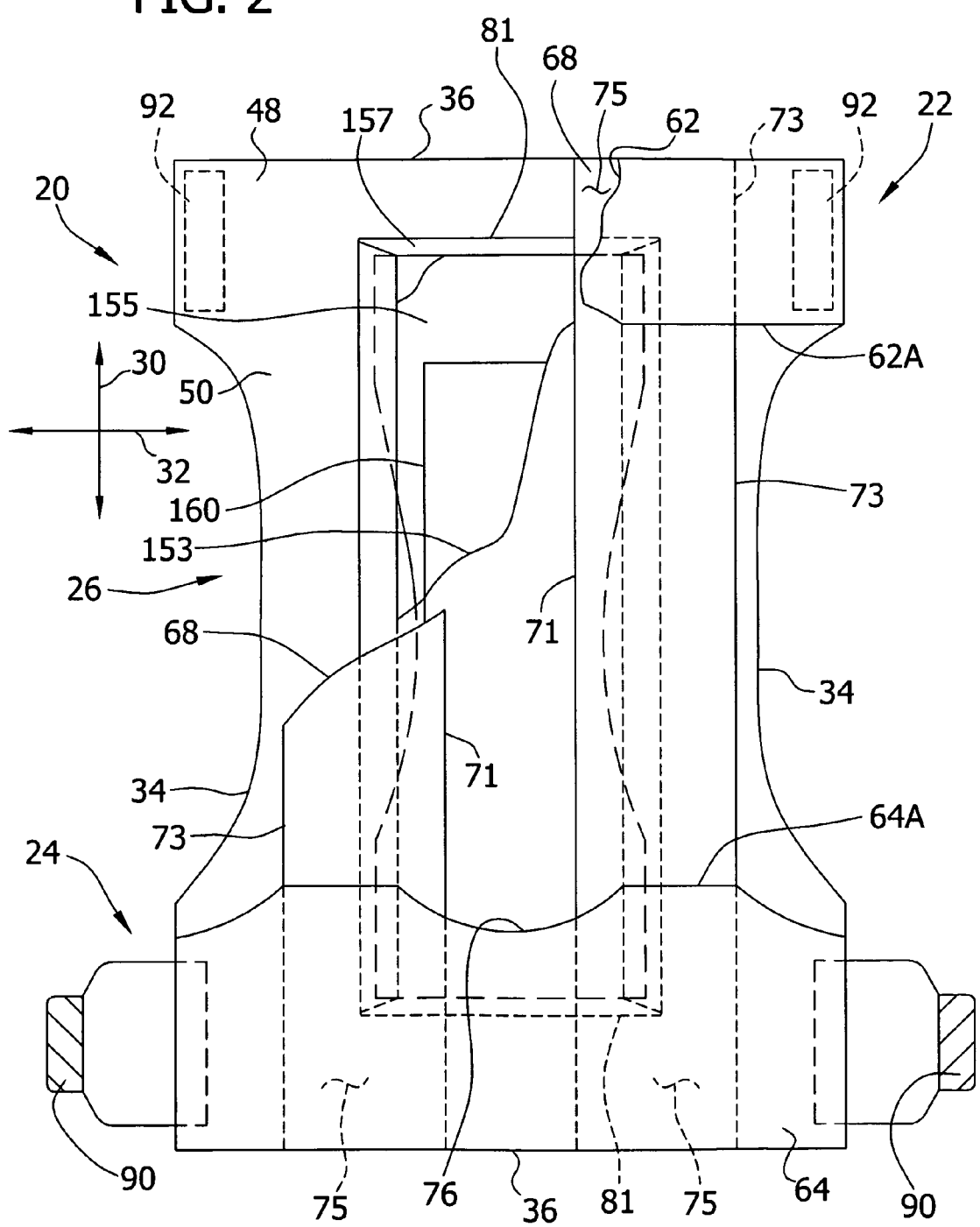
FIG. 2 is a top plan view similar to FIG. 1 but with portions cut away to reveal internal construction.

With reference to the drawings and in particular to FIGS. 1 and 2, a disposable garment according to one embodiment of the present invention is described herein with reference to a disposable absorbent garment, and more particularly to a diaper, generally indicated at 20, intended to be worn about the waist and lower torso of an infant or toddler. It is understood, however, that the various aspects of the present invention are equally adaptable to other types of disposable garments such as adult incontinence garments, training pants, disposable swim pants and feminine hygiene garments. Disposable garments as referenced herein are intended for limited periods of use and are otherwise not intended for laundering. A disposable diaper, for example, is discarded after soiling by the wearer. Optionally, a disposable garment may include a replaceable absorbent insert wherein the remaining components of the garment may be reused several times before discarding.

The disposable diaper 20 of the illustrated embodiment generally has a front waist region 22, a back waist region 24, and a center region, otherwise referred to herein as a crotch region 26, extending longitudinally between and interconnecting the front and back waist regions. The front and back waist regions 22, 24 comprise those portions of the diaper 20 which, when worn, wholly or partially cover or encircle the waist and/or mid-lower torso of the wearer. The crotch region 26 generally is that portion of the diaper 20 which, when worn, is positioned between the legs of the wearer and covers the lower torso and crotch of the wearer.

The diaper 20 has a longitudinal direction 30 and a lateral direction 32 thereof perpendicular to the longitudinal direction as indicated by the directional arrows provided in FIG. 1. The diaper also has a "z-direction" 33 (FIG. 3) which is generally normal to the longitudinal direction 30 and lateral direction 32. The various components of the diaper 20 described herein suitably define an inner surface 52 (FIG. 1) (otherwise referred to herein as a body facing surface) which faces the wearer of the diaper and an outer surface 54 (FIG. 3)(otherwise referred to herein as a garment facing surface) which faces away from the wear.

With further reference to FIG. 1, the diaper 20 also has a pair of laterally opposite side edges 34, and a pair of longitudinally opposite ends 36. The diaper 20 is illustrated in FIGS. 1 and 2 in an unfolded and laid flat (e.g., uncontracted) condition, similar to the configuration of the diaper prior to it being placed on the wearer. As worn, the diaper takes on a three-dimensional configuration (not shown) in which the side edges 34 of the diaper suitably define leg openings of the diaper 20 and the ends 36 together define a waist opening of the diaper 20.

The diaper 20 may be of various suitable shapes when unfolded and laid flat. For example, the diaper 20 may have an overall rectangular shape, T-shape, hour-glass shape or a general I-shape as in the illustrated embodiment. Examples of diaper configurations suitable for use in connection with the instant application are described in U.S. Pat. No. 4,798,603 issued Jan. 17, 1989 to Meyer et al.; U.S. Pat. No. 5,176,668 issued Jan. 5, 1993, to Bernardin; U.S. Pat. No. 5,176,672 issued Jan. 5, 1993 to Bruemmer et al.; U.S. Pat. No. 5,192,606 issued Mar. 9, 1993 to Proxmire et al.; and U.S. Pat. No. 5,509,915 issued Apr. 23, 1996 to Hanson et al., the disclosures of which are hereby incorporated by reference. The various aspects and configuration of the invention can provide distinctive combinations of softness, body conformity, reduced red-marking of the wearer's skin, reduced hydration, and improved containment of body exudates.

Figure 3:
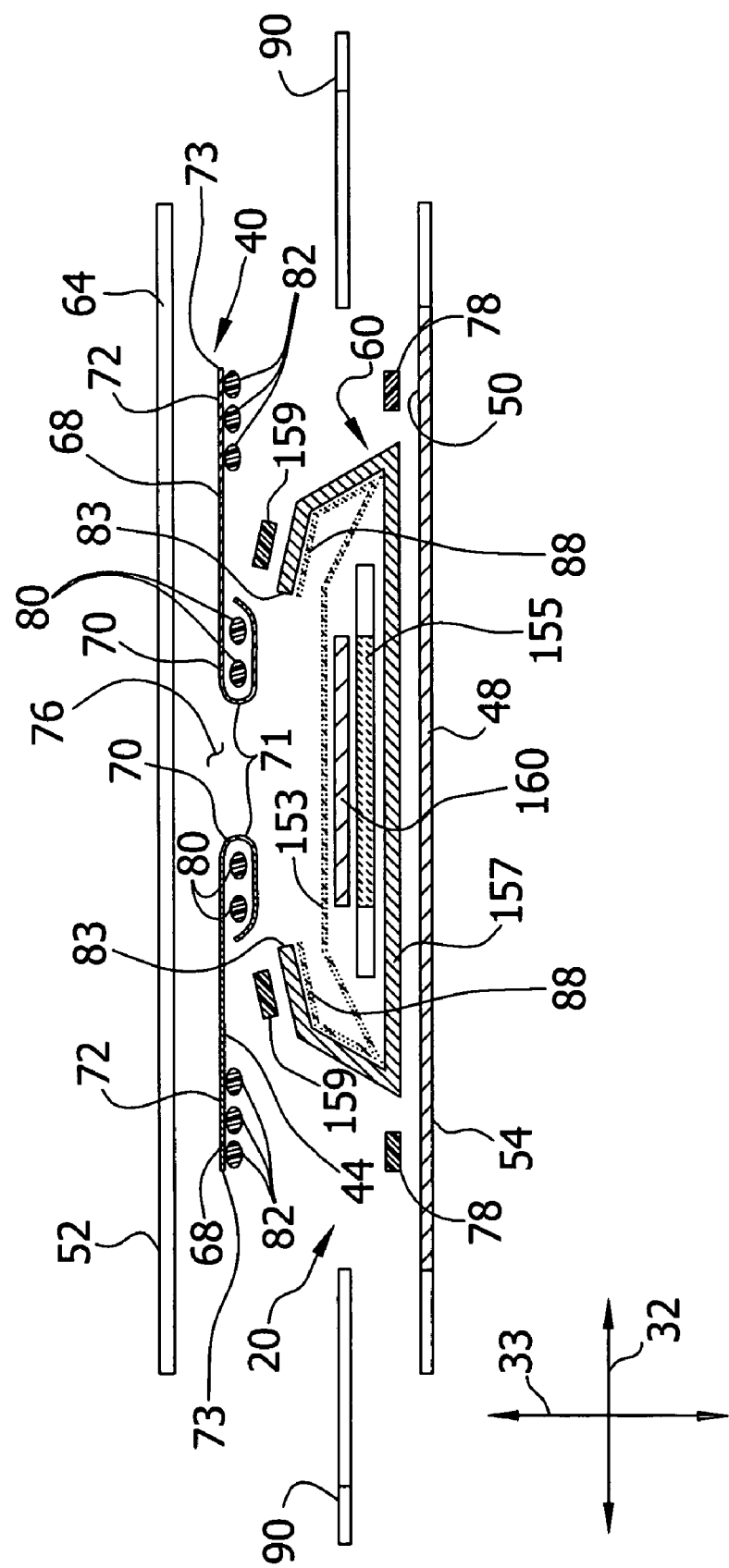
FIG. 3 is an exploded cross-section taken in the plane of line 3-3 in FIG. 1.

The illustrated diaper 20 suitably comprises an inner layer, generally indicated at 40, an outer layer, generally indicated at 48 in generally opposed (and more suitably superposed) relationship with the inner layer, and an absorbent assembly, generally indicated at 60, disposed between the inner and outer layers of the diaper for taking in and retaining body exudates released by the wearer. The inner layer 40 has an inner, or body facing surface that at least in part defines the inner surface 52 of the diaper 20 and an outer, or garment facing surface 44 (FIG. 3). The outer layer 48 (also commonly referred to as an outer cover) has an inner, or body facing surface 50 (FIGS. 2 and 3) and an outer or garment facing surface that defines the outer surface 54 of the diaper 20.

The inner layer 40 of the illustrated embodiment of FIG. 1 is suitably of a multiple component construction, and in particular comprises a front waist panel 62 (broadly, a first end panel of the inner layer) at least in part defining the front waist region 22 of the diaper 20 and a back waist panel 64 (broadly a second end panel of the inner layer) at least in part defining the rear waist region 24 of the diaper. The front and back waist panels 62, 64 are suitably longitudinally spaced from each other. For example, in the illustrated embodiment of FIG. 1 the front waist panel has a longitudinally outer end coterminous with the outer layer 48 to define a longitudinal end 36 of the diaper 20, and a longitudinally inner end 62A. The back waist panel 64 has a longitudinally outer end coterminous with the opposite end of the outer layer to define the opposite longitudinal end 36 of the diaper 20, and a longitudinally inner end 64A spaced longitudinally from the inner end 62A of the front waist panel so that the spacing therebetween at least in part defines the crotch region 26 of the diaper.

The inner layer 40 further comprises a pair of laterally spaced side panels 68 that extend longitudinally through the crotch region 26 of the diaper 20, and more suitably extend from the front waist region 22 through the crotch region to the back waist region 24 of the diaper, and ever more suitably from one end 36 of the diaper 20 to the other end. Thus, it will be seen that the front and back waist panels 62, 64 and laterally spaced side panels 68 together define a central opening 76 of the inner layer 40 of the diaper 20 through which liquid, semi-liquid and solid exudates released by the wearer pass to the absorbent assembly 60. Each of the side panels 68 has a laterally inboard edge 71 and a laterally outboard edge 73. In the illustrated embodiment, the side edges of the front and back waist panels 62, 64 and the side edges of the outer layer 40 are coterminous and together define the lateral side edges 34 of the diaper 20 while the longitudinally inner ends 62A, 64A of the front and back waist panels 62, 64 and laterally inboard edges 71 of the side panels 68 together define the central opening 76 of the inner layer 40 of the diaper.

In one suitable embodiment, illustrated in FIG. 1, the side panels 68 of the inner layer 40 are formed separate from the front and back waist panels 62, 64 of the inner layer 40 and extend longitudinally from one longitudinal end 36 of the diaper 20 (i.e., the outer end of the front waist panel) to the opposite longitudinal end of the diaper (i.e., the outer end of the back waist panel). Accordingly, longitudinal end margins 75 of the side panels 68 generally underlie the front and back waist panels 62, 64 in the front and back waist regions 22, 24 of the diaper 20. The side panels 68 are suitably secured to the front and back waist panels 62, 64 along all or part of the end margins 75 of the side panels. More suitably, the side panels 68 are secured to the front and back waist panels 62, 64 along the laterally inboard edge 71 and/or a region adjacent thereto of each side panel end margin 75 that underlies the front and back waist panels. Accordingly, the outboard edges 73 of the side panels 68 may be unsecured to the front and back waist panels 62, 64. In another embodiment (not shown) the side panels 68 may be secured to the front and back waist panels 62, 64 only across the longitudinally outer ends of the front and back waist panels corresponding to the longitudinal ends 36 of the diaper 20.

In one suitable embodiment, illustrated in FIG. 3, the side panels 68 are suitably secured to the outer cover 48 by adhesive 78 generally at and/or adjacent the laterally outboard edges 73 of the side panels. The adhesive 78 may be applied as a uniform continuous layer of adhesive, a patterned layer of adhesive, a sprayed pattern of adhesive, an array of separate lines, swirls or dots of adhesive, or any other pattern of adhesive. As further discussed herein, the side panels 68 and the outer layer 48 are stretchable in the lateral direction so that the attachment of the side panels to the outer layer does not inhibit the stretchability of either the side panels or the outer layer. Further, the laterally inboard edge 71 of the side panels 68 is free from attachment to the outer layer 48 so that the inboard edge of the side panels is positionable relative to and independent of the outer layer.

It is understood, however, that the side panels 68 need not extend to the longitudinal ends 36 of the diaper 20 to remain within the scope of this invention. For example, the side panels 68 may only be sized in length to underlie a portion of each of the front and back waist panels but otherwise terminate longitudinally inward of the ends 36 of the diaper 20. It is also contemplated that the side panels 68 may instead be sized in length to extend longitudinally into abutting (e.g., end-to-end) relationship with the longitudinally inner ends 62A, 64A of the front and back waist panels 62, 64 and be secured thereto without departing from the scope of this invention.

The front and back waist panels 62, 64 of the inner layer 40 are suitably compliant, soft feeling, and nonirritating to the wearer's skin. The waist panels 62, 64 may have any suitable shape, such as rectangular (e.g., the front waist panel of the illustrated embodiment), trapezoidal or otherwise non-rectangular (e.g., the back waist panel of the illustrated embodiment) depending on the desired overall shape of the diaper 20. One or both of the front and back waist panels 62, 64 may extend laterally outward beyond laterally outboard edges 73 (FIG. 3) of the connecting members 68 as illustrated in FIG. 1. It is understood, however, that the side edges of the front and back waist panels 62, 64 may instead be coterminous with the laterally outboard edges 73 of the connecting members 68 and remain within the scope of this invention.

The front and back waist panels 62, 64 may be suitably constructed to be vapor and liquid permeable, vapor permeable but liquid impermeable, or vapor and liquid impermeable. For example, the front and back waist panels 62, 64 may be suitably constructed of any of the liquid permeable materials from which a topsheet 153 of the absorbent assembly 60 is constructed as described later herein. As another example, the front and back waist panels 62, 64 may be suitably constructed of any of the materials from which a backsheet 157 of the absorbent assembly is constructed as is also described later herein.

In particularly suitably embodiments, the front and back waist panels 62, 64 are also suitably stretchable, and are more suitably elastic (i.e., elastomerically stretchable) in at least the lateral direction of the diaper 20 to provide a retractive force about the waist of the diaper wearer. It is contemplated that the front and back waist panels 62, 64 may also be stretchable, and may even be elastic, in the longitudinal direction of the diaper.

As used herein, the term "stretchable" refers to a material that may be extensible or elastomeric. That is, the material may be extended, deformed or the like, without breaking, and may or may not significantly retract after removal of an extending force. The terms "elastomeric" or "elastic" are used interchangeably herein and refer to that property of a material where upon removal of an elongating force, the material is capable of recovering to substantially its unstretched size and shape or the material exhibits a significant retractive force. The term "extensible" refers to that property of a material where upon removal of an elongating force, the material experiences a substantially permanent deformation or the material does not exhibit a significant retractive force. In particular, elastomeric materials utilized in connection with the present invention may be elongated/extended or stretched in at least one direction without breaking by at least 25% (to at least 125% of its initial unstretched length) in at least one direction, suitably by at least 50% (to at least 150% of its initial unstretched length) and which will recover, upon release of the applied stretching or biasing force, at least 10% of their elongation. It is generally suitable that the elastomeric material or composite be capable of being elongated by at least 100%, more suitably by at least 200%, of its relaxed length and recover at least 30% and more suitably 50% of its elongation upon release of a stretching, biasing force, within about one minute.

Similarly, extensible or elongatable materials of the present invention may be capable of stretching in at least one direction without breaking by at least 25% (to at least 125% of its initial unstretched length) in at least one direction, suitably by at least 50% (to at least 150% of its initial unstretched length), more suitably by at least 100% (to at least 200% of its initial unstretched length). As an example, an extensible material having an initial unstretched length of 3 inches (7.6 centimeters) may be stretched without breaking to a stretched length of at least 3.75 inches (9.5 centimeters) in at least one direction (for the "by at least 25%" value).

Various materials may be used to construct the stretchable front and back waist panels 62, 64. For example, in one suitable embodiment each of the panels 62, 64 are elastic and comprise a three ply laminate such as a Stretch Bonded Laminate (SBL) that consists of two nonwoven facings attached to an elastic inner layer while the inner layer is in a stretched condition. One such suitable SBL material is disclosed in U.S. Pat. No. 4,657,802 to Morman, incorporated by reference herein.

Another suitable embodiment of the elastic panels 62, 64 is a Necked Bonded Laminate (NBL) that is also a three-ply laminate but the elastic inner layer is not prestretched prior to attaching the two nonwoven facings. For the NBL, the nonwoven facings are necked stretched and the elastic inner layer is attached between the necked facings. Other suitable elastically stretchable NBL materials as are described in U.S. Pat. No. 5,226,992 issued on Jul. 13, 1993 to Morman, the disclosure of which is hereby incorporated by reference.

In other embodiments the panels 62, 64 may be formed from elastically stretchable film materials. Such films may be elastic in the lateral direction, the longitudinal direction or both. One suitable elastic film is a breathable elastic film as described in U.S. patent application Ser. No. 10/703,761 filed on Nov. 7, 2003 and titled "Microporous Breathable Elastic Films, Methods of Making Same, And Limited Use or Disposable Product Applications", the disclosure of which is hereby incorporated by reference. Use of such breathable, elastic films may provide additional benefits for the skin health of the wearers of the garments of the invention.

Additional examples of suitable breathable elastic film laminates for use in constructing the front and back waist panels 62, 64 are described in Provisional U.S. Patent Application Ser. No. 60/518,100 filed on Nov. 7, 2003 and titled "Microporous Breathable Elastic Film Laminates, Methods of Making Same, and Limited Use or Disposable Product Applications", the disclosure of which is hereby incorporated by reference. Other suitable elastic laminates are described in U.S. patent application Ser. No. 10/743,245 filed on Dec. 22, 2003 and titled "Extensible and Stretch Laminates and Method of Making Same", the disclosure of which is hereby incorporated by reference.

Other suitable elastic nonwoven materials from which the front and back waist panels 62, 64 may be constructed include elastomeric materials that are treated using nonwoven manufacturing processes such as meltblowing. Suitable elastomers that may be formed into microfibers/nonwoven webs are described in U.S. Pat. No. 4,663,220 issued to Wisneski et al. on May 5, 1987 and titled "Polyolefin-Containing Extrudable Compositions and Methods for Their Formulation Into Elastomeric Products Including Microfibers", the disclosure of which is hereby incorporated by reference. Meltblowing of KRATON copolymers ("KRATON" is a trade designation of the Shell Chemical Company) to form composite nonwoven elastic webs is described in U.S. Pat. No. 4,657,802 issued to Morman on Apr. 14, 1987 and titled "Composite Nonwoven Elastic Web", the disclosure of which is hereby incorporated by reference.

The side panels 68 are formed separate from the front and back waist panels 62, 64 and absorbent assembly 60 for subsequent assembly therewith. The side panels 68 are suitably constructed to be generally compliant, soft feeling, and nonirritating to the wearer's skin. In one particularly suitable embodiment, each side panel 68 is stretchable (e.g., at least extensible), and is more suitably elastic, in the longitudinal direction 30 of the diaper 20. It will be seen, then, that the combination of the at least laterally stretchable front and back waist panels 62, 64 with the at least longitudinally stretchable side panels 68 provides the inner layer 40 of the diaper with biaxial (e.g., lateral and longitudinal) stretch capabilities.

In another suitable embodiment, each side panel 68 is additionally stretchable (e.g., at least extensible), and may even be elastic, in the lateral direction 32 of the diaper 20. Providing lateral direction 32 stretchability to the side panel reduces the limiting effect that securing the side panel edge margins 75 to the front and back waist panels 62, 64 may have on the lateral stretch properties of the front and back waist panels. The lateral direction stretch capabilities of the side panel 68 also permit the side panel to stretch laterally during use at least along the longitudinal segment of the side panel extending between the longitudinally inner ends 62A, 64A of the front and back waist panels 62, 64, e.g., independent of the absorbent assembly, the outer layer and the front and back waist panels.

In the illustrated embodiment, each side panel 68 suitably comprises an elongate strip, such as a woven material, nonwoven material, film or laminate comprises of one or more layers of such material. As an example, the side panels 68 may be suitably constructed of any of the materials from which a topsheet 153 or backsheet 157 of the absorbent assembly 60 may be constructed as described later herein. The side panels 68 are suitably constructed to be vapor permeable and liquid impermeable. However, the side panels 68 may alternatively be vapor and liquid impermeable, or vapor and liquid permeable, within the scope of this invention.

Each of the side panels 68 is suitably rendered elastic (e.g. elastomerically stretchable) in the longitudinal direction by securing one or more longitudinally extending elastic members along all or part of the length of the side panels. As an example, in the illustrated embodiment of FIG. 3, the elastic members comprise elastic strands 80, 82 such as are known for use with containment flaps, waist elastics and leg cuffs of conventional disposable garments such as diapers. In particular, one elastic member comprises a pair of elastic strands 80 extending longitudinally adjacent the laterally inboard edge 71 of the side panel 68. The strip of material to which the elastic strands 80 are secured is folded over at the laterally inboard edge 71 of the side panel 68 to enclose the elastic strands therein. The elastic strands 80 suitably extend at least along the segment of the side panel 68 between the longitudinally inner ends 62A, 64A of the front and back waist panels 62, 64, but may extend along a greater or lesser extent of the length of the side panel. The elastic strands 80 (broadly, the elastic member) are suitably secured to the strip of material while the elastic strands are in a stretched condition.

Another elastic member of the side panel 68 comprises three elastic strands 82 extending longitudinally of the side panel in laterally spaced relationship with the elastic strands 80, and more suitably adjacent the laterally outboard edge 73 of the side panel 68. As illustrated in FIG. 3, the elastic strands 82 are secured to the garment facing side of the strip of material and the strip such that upon securement of the outboard edge 73 of the side panel 68 to the outer layer the elastic strands are enclosed therebetween. It is understood, however, that the outboard edge 73 of the side panel 68 may suitably fold over the strands 82. The elastic strands 82 suitably extend longitudinally at least along the segment of the side panel 68 between the longitudinally inner ends 62A, 64A of the front and back waist panels 62, 64, but may extend along a greater or lesser extent of the length of the side panel. The elastic strands 82 (broadly, the elastic member adjacent the outboard edge 73 of the side panel 68) are suitably secured to the strip of material while the elastic strands are in a stretched condition.

While in the illustrated embodiment the elastic member defined by the elastic strands 82 extends longitudinally substantially the same length as the elastic member defined by the elastic strands 80, it is understood that the length of the elastic member adjacent the outboard edge 73 (strands 82) of the side panel 68 may be different from the length of the elastic member adjacent the inboard edge 71 and remain within the scope of this invention. Also, while the elastic members are illustrated in FIG. 3 as comprising one or more elastic strands 80, 82, it is contemplated that the elastic members may be other than elastic strands, such as wider elastic bands or other suitable elastic members, without departing from the scope of this invention. It is further understood that the stretchability and elasticity of the elastic member adjacent the inboard edge 71 of the side panel 68 may be different from the stretchability and elasticity of the elastic member adjacent the outboard edge 73 of the side panel.

In other embodiments, the side panel 68 may have only one elastic member adjacent the outboard edge 73 of the side panel, e.g., with the elastic member adjacent the inboard edge of the side panel being omitted, without departing from the scope of this invention. It is also contemplated that the entire connecting member may be constructed of an elastic material, such as any of the elastic materials from which the front and back waist panels 62, 64 may be constructed.

With particular reference to FIGS. 2 and 3, the absorbent assembly 60 has longitudinally opposite ends 81 and laterally opposite side edges 83, and is disposed below the central opening 76 of the inner layer 40, e.g., in the crotch region 26 of the diaper 20, to receive body exudates that pass through the inner layer. The absorbent assembly 60 is suitably sized in length to be shorter than the overall length of the diaper 20 but to otherwise extend longitudinally at least up to and more suitably beyond the longitudinally inner ends 62A, 64A of the front and back waist panels 62, 64 (e.g., sized in length at least equal to and more suitably longer than the central opening 76 of the inner layer 40). The absorbent assembly 60 is also suitably sized in width to be slightly narrower than the overall width of the diaper 20 at the crotch region 26, but to otherwise extend laterally at least up to and more suitably laterally outward of the laterally inboard edges 71 of the side panels 68 (e.g., sized as wide as and more suitably wider than the central opening of the inner layer. It is understood, however, that the absorbent assembly 60 may extend longitudinally to the longitudinal ends 36 of the diaper 20 and/or laterally to the side edges 34 of the diaper without departing from the scope of this invention.

The illustrated absorbent assembly 60 suitably comprises the topsheet 153, the backsheet 157 and an absorbent structure 155 disposed therebetween for taking in and retaining liquid body exudates (e.g. urine where the garment is the diaper 20). In particular, the topsheet 153 and backsheet 157 are suitably in opposed, generally coextensive relationship with each other so that they together define longitudinal ends 81 and lateral side edges 83 of the absorbent assembly. It is contemplated, however, that the topsheet 153 and backsheet 157 need not be coextensive, e.g., one may be longer and/or wider than the other to singly define the longitudinal ends 81 and/or lateral side edges 83 of the absorbent assembly 60 without departing from the scope of this invention.

The topsheet 153 of the absorbent assembly 60 suitably defines an inner or body facing surface of the absorbent assembly that is compliant, soft feeling, and nonirritating to the wearer's skin since it is exposed to the wearer's skin through the central opening 76 of the inner layer 40. Further, the topsheet 153 may be less hydrophilic than the absorbent structure 155, and is sufficiently porous to be liquid permeable so that liquid body exudates can readily penetrate through the topsheet to the absorbent structure 155. The topsheet 153 may be suitably formed from a wide selection of web materials, such as porous foams, reticulated foams, apertured plastic films, natural fibers (for example, wood or cotton fibers), synthetic fibers (for example, polyester or polypropylene fibers), or a combination of natural and synthetic fibers.

In particular, various woven and nonwoven fabrics may be used for the topsheet 153. For example, the topsheet 153 may be formed of a meltblown or spunbond web of polyolefin fibers. The topsheet layer 153 may also be a bonded-carded web composed of natural and/or synthetic fibers. The topsheet 153 may be composed of a substantially hydrophobic material, and the hydrophobic material may, optionally, be treated with a surfactant or otherwise processed to impart a desired level of wettability and hydrophilicity. As one example, the topsheet layer 153 may suitably comprise a nonwoven, spunbond, polypropylene fabric composed of about 2.8-3.2 denier fibers formed into a web having a basis weight of about 22 grams per square meter and a density of about 0.06 grams per cubic centimeter. The web can be treated with a suitable surfactant, such as about 0.28% Triton X-102 surfactant, which may be applied by any conventional means such as spraying, printing, brush coating or the like.

The backsheet 157 is suitably constructed to be liquid impermeable and may or may not be vapor permeable. For example, the backsheet 157 may be formed from a thin plastic film or other flexible liquid-impermeable material. In a more particular example, the backsheet 157 may be formed from a polyethylene film having a thickness of from about 0.013 millimeter (0.5 mil) to about 0.051 millimeter (2.0 mils). The backsheet 157 may also be formed from a polyolefin film having a nonwoven web laminated to the exterior surface thereof, such as a spunbond web of polyolefin fibers. For example, a stretch-thinned polypropylene film having a thickness of about 0.015 millimeter (0.6 mil) may be thermally laminated to a spunbond web of polypropylene fibers having a fiber diameter of about 15 to 20 microns, with the nonwoven web having a basis weight of about 17 grams per square meter (0.5 ounce per square yard). The backsheet 157 may in some embodiments include bicomponent fibers such as polyethylene/polypropylene bicomponent fibers. The backsheet 157 may also include a vapor permeable non-woven facing layer laminated to a micro-porous film to impart "breathability" to the barrier layer. Suitable "breathable" barrier layer 157 materials are described in U.S. Pat. No. 5,695,868 issued Dec. 9, 1997 to McCormack et al. and U.S. Pat. No. 5,843,056 issued Dec. 1, 1998 to Good et al., the disclosures of which are incorporated by reference to the extent they are consistent herewith.

The backsheet 157 may also be constructed of any of the materials disclosed later herein from which the outer layer 48 of the diaper 20 may be constructed. While the backsheet 157 may even be constructed of the same material as the outer layer 48, it is contemplated that the backsheet 157 and outer layer 48 may be constructed of different materials and remain within the scope of this invention. In particular, for example, the backsheet 157 need not have a non-woven or otherwise soft-textured outer surface because it is substantially covered by the outer layer 48 of the diaper 20 and therefore unexposed exterior of the diaper. Other suitable backsheet 157 constructions are disclosed in U.S. Pat. No. 6,217,563 (Van Gompel et al.), the disclosure of which is incorporated by reference to the extent it is consistent herewith. The backsheet 157 may optionally be stretchable, and may further optionally be elastic.

The absorbent structure 155 of the absorbent assembly 60 may suitably comprise a matrix of hydrophilic fibers, such as a web of cellulosic fluff, and may optionally further comprise a high-absorbency material commonly known as superabsorbent material. For example, the absorbent structure 155 may include a matrix of cellulosic fluff, such as wood pulp fluff, and superabsorbent hydrogel-forming particles. The wood pulp fluff may be exchanged with synthetic, polymeric, meltblown fibers or with a combination of meltblown fibers and natural fibers. The superabsorbent particles may be substantially homogeneously mixed with the hydrophilic fibers or may be nonuniformly mixed. Alternatively, the absorbent structure 155 may include a laminate of fibrous webs and superabsorbent material or other suitable matrix for maintaining a superabsorbent material in a localized area. The size and the absorbent capacity of absorbent structure 155 should be compatible with the size of the intended wearer and the liquid loading imparted by the intended use of the garment. Further, the size and the absorbent capacity of the absorbent structure 155 can be varied to accommodate disposable absorbent garment wearers ranging from infants through adults.

The high-absorbency material may be selected from natural, synthetic, and modified natural polymers and materials. The high-absorbency materials may be inorganic materials, such as silica gels, or organic compounds, such as crosslinked polymers. The term "crosslinked" refers to methods for effectively rendering normally water-soluble materials substantially water insoluble but swellable. Such methods include, for example, physical entanglement, crystalline domains, covalent bonds, ionic complexes and associations, hydrophilic associations such as hydrogen bonding, and hydrophobic associations or Van der Waals forces. Examples of synthetic, polymeric, high-absorbency materials include the alkali metal and ammonium salts of poly(acrylic acid) and poly(methacrylic acid), poly(acrylamides), poly(vinyl ethers), maleic anhydride copolymers with vinyl ethers and alpha-olefins, poly(vinyl pyrrolidone), poly(vinyl morpholinone), poly(vinyl alcohol), and mixtures and copolymers thereof. Further polymers suitable for use in the absorbent structure 155 include natural and modified natural polymers, such as hydrolyzed acrylonitrile-grafted starch, acrylic acid grafted starch, methyl cellulose, carboxymethyl cellulose, hydroxypropyl cellulose, and the natural gums, such as alginates, xanthan gum, locust bean gum, and the like. Mixtures of natural and wholly or partially synthetic absorbent polymers may also be useful. The high absorbency material may be in any of a wide variety of geometric forms. As a general rule, the high absorbency material is in the form of discrete particles. However, the high absorbency material may also be in the form of fibers, flakes, rods, spheres, needles, or the like.

In general, the high-absorbency material is suitably present in the absorbent structure 155 in an amount from about 5 to about 90 percent by weight, more suitably in an amount of at least about 30 percent by weight, and even more suitably in an amount of at least about 50 percent by weight based on a total weight of the absorbent structure 155. For example, in a particular aspect, the absorbent structure 155 may comprise a laminate which includes at least about 50 percent by weight and more suitably at least about 70 percent by weight of high-absorbency material overwrapped by a fibrous web or other suitable material for maintaining the high-absorbency material in a localized area. An example of high-absorbency material suitable for use in the present invention is DRYTECH 2035 polymer available from Dow Chemical, a business having offices in Midland, Mich. Other suitable superabsorbents may include FAVOR SXM 880 polymer obtained from Stockhausen, a business having offices in Greensboro, N.C.

The absorbent structure 155 may further comprise a wrap sheet (not shown) at least covering the body facing surface of the fibrous matrix, and more suitably enclosing the matrix in the wrapsheet. Alternatively, the wrapsheet may cover both the body facing surface and the garment facing surface of the matrix but not the sides of the matrix. The wrapsheet is suitably comprised of an absorbent material, or at least a liquid permeable material. For example, a suitable wrapsheet may comprise a meltblown web composed of meltblown fibers, such as meltblown polypropylene fibers. Another example of a suitable wrapsheet may comprise a low porosity cellulosic web, such as a tissue web composed of an approximately 50/50 blend of hardwood/softwood fibers.

Figure 6:
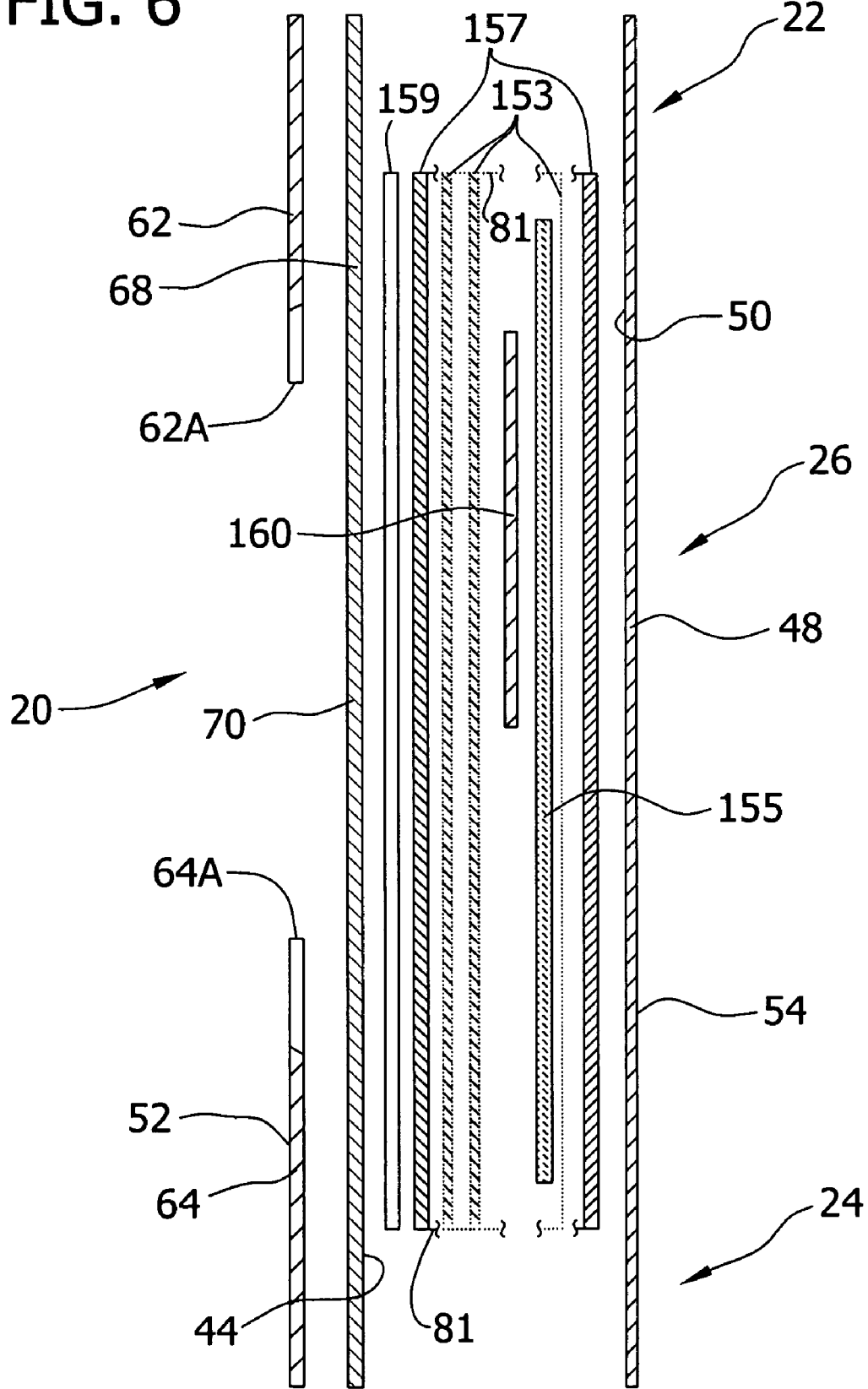
FIG. 6 is an exploded cross-section taken in the plane of line 6-6 of FIG. 1.

With reference to FIGS. 2 and 6, the absorbent assembly 60 may further include a surge management layer 160 positioned between the topsheet 153 and the absorbent structure 155 to quickly take in and efficiently distribute liquid exudates to the absorbent structure 155. Suitable constructions and arrangements of surge management layers are well known to those skilled in the art. The surge management layer 160 is sized narrower than the width of the absorbent structure 155 and is sized substantially shorter than the length of the absorbent structure. The surge layer 160 is suitably positioned longitudinally nearer to the front end of the absorbent assembly where initial insults occur.

As illustrated in FIG. 3, the topsheet 153 and backsheet 157 of the absorbent assembly 60 may extend laterally beyond the side edges of the absorbent structure 155 to the side edges 83 of the absorbent assembly 60. That is, the width of the absorbent structure is less than the width of the topsheet 153 and/or backsheet 157 so that the side edges 83 of the absorbent assembly 60 are disposed laterally outward of the side edges of the absorbent structure. In particular embodiments, the topsheet 153 and backsheet 155 are suitably secured to each other along the longitudinal ends 81 and lateral side edges 83 of the absorbent assembly 60 by adhesive bonding, ultrasonic bonding, thermal bonding or other suitable securement technique. The topsheet 153 may be secured directly to the backsheet 157 as in the illustrated embodiment or indirectly, such as by an intermediate component.

The laterally outward extensions of the topsheet 153 and/or the backsheet 157 are suitably C-folded as illustrated in FIG. 3 such that lateral edge margins 88 of the absorbent assembly 60 (e.g., a lateral region at and/or adjacent to the side edges 83 of the absorbent assembly), and more suitably the garment facing surface thereof, are in opposed relationship with the inner layer 40 of the diaper 20 for attachment thereto as will be described later herein. In particular, the outer or garment facing surface of the absorbent assembly 60 at the lateral edge margins 88 thereof (e.g., the outer surface of the backsheet 157) are in opposed relationship with and secured to the outer or garment facing surface 44 of the inner layer 40 and more suitably the side panels 68 of the inner layer. It is contemplated that the lateral extensions of the topsheet 153 and/or the backsheet 155 may instead be Z-folded or folded in another suitable manner which allows subsequent unfolding, or expansion, of the lateral extensions during loading of the absorbent assembly 60. It is also contemplated that the lateral extensions of the topsheet 153 and/or backsheet 155 may be folded such that the inner or body facing surface of the absorbent assembly at the lateral edge margins 88 thereof are in opposed relationship with and secured to the garment facing surface 44 of the inner layer 40.

The lateral extensions of the topsheet layer 153 and the barrier layer 157 allow the absorbent assembly 60 to expand in the z-direction 33 (FIG. 3) upon loading of the absorbent structure 155. The lateral extensions also allow for lateral expansion of the absorbent assembly 60 upon lateral elongation of the inner layer opening 76, such as where the front and back waist panels 62, 64 are stretched laterally and thus move the side panels 68 further apart.

With particular reference still to FIG. 3, the lateral edge margins 88 of the absorbent assembly 60 are suitably secured to the side panels 68 by adhesive 159. The adhesive 159 may be applied as a uniform continuous layer of adhesive, a patterned layer of adhesive, a sprayed pattern of adhesive, an array of separate lines, swirls or dots of adhesive, or any other pattern of adhesive. It is understood that the lateral edge margins 88 of the absorbent assembly 60 may alternatively, or additionally be secured to the side panels 68 by ultrasonic bonding, thermal bonding or other suitable securement techniques.

The absorbent assembly 60 is also suitably secured along its longitudinal ends to the respective front and back waist panels 62, 64. The absorbent assembly 60 is otherwise free from securement to the front and back waist panels 62, 64 laterally between the side panels 68 particularly along the longitudinally inner ends 62A, 64A of the waist panels. In this manner, the front and back waist panels 62, 64 and the absorbent assembly 60 together form longitudinally opposite pockets during wear (e.g., that open longitudinally inward of the diaper 20) for collecting liquid, semi-liquid and solid exudates.

In a particularly suitable embodiment such as that illustrated in FIGS. 3 and 6, the lateral edge margins 88 of the absorbent assembly 60 are secured to the side panels 68 along a line of attachment, e.g., defined by the adhesive 159 in the illustrated embodiment, that extends generally longitudinally of the side panels along at least a longitudinal segment thereof and more suitably along the entire length of the side panels. It is further understood that the adhesive 159 may extend longitudinally of the side panels 68 only along the longitudinal length of the absorbent assembly 60 without departing from the scope of the invention. The line of attachment is suitably disposed laterally between the inboard and outboard edges 71, 73 of the side panel 68. In this manner, at least a longitudinal segment of each side panel 68, such as the segment that extends between the longitudinally inner ends 62A, 64A of the front and back waist panels 62, 64, is what is referred to herein as being hinged relative to the absorbent assembly 60 and waist panels about a longitudinal axis defined by the line of attachment. That is, the inboard and outboard edges 71, 73 of the side panels 68 are freely positionable relative to the absorbent assembly, e.g., about the line of attachment, without moving, expanding or otherwise reconfiguring the absorbent assembly.

Because the inboard edges 71 of the side panels 68 are otherwise unsecured to the outer layer or other components of the diaper 20 at least along the segment of the side panels extending between the inner ends 62A, 62B of the waist panels 62, 64, the inboard edges of each side panel along such a segment are also positionable relative to and independent of the outer layer and the front and back waist panels. Likewise, the outboard edges 73 of the side panels 68 are unsecured to the front and back waist panels 62, 64 at least along the segment of the side panels extending between the inner ends 62A, 62B of the waist panels, the outboard edges of each side panel along such a segment are also positionable relative to and independent of the front and back waist panels.

In this configuration, the line of attachment between each side panel 68 and the edge margin 88 of the absorbent assembly 60 generally defines a laterally inner portion 70 or flap portion of the side panel between the line of attachment and the inboard side edge 71 of the side panel, and a laterally outer portion 72 or leg cuff portion of the side panel between the line of attachment and the outboard side edge 73 of the side panel. In this manner, during wear the inner portion 70 of each side panel 68 broadly defines a containment flap along at least the longitudinal segment of the side panel between the longitudinally inner ends 62A, 64A of the front and back waist panels 62, 64. In particular, the containment flaps are oriented laterally inward and generally upright in the crotch region 26 to inhibit the lateral flow of body exudates out of the diaper 20. The outer portions 72 of the side panels 68 broadly define leg cuffs that are oriented laterally outward and generally downward to gasket about the wearer's legs to thereby reduce leakage and provide improved comfort and appearance.

Because the side panels 68 are generally hinged to the expandable absorbent assembly 60, upon wearing of the diaper 20 the containment flap portion (e.g., laterally inner portion 70) of the side panel is able to freely move relative to the absorbent assembly, the front and back waist panels 62, 64 and outer layer 48 up to its generally upright orientation at the crotch of the wearer while the leg cuff portion (e.g., laterally outer portion 72) of the side panel is able to freely move relative to the absorbent assembly and the front and back waist panels 62, 64 to a lower position nearer the thigh of the wearer. Where the side panels 68 are constructed to also be stretchable in the lateral direction, because the leg cuff portion (e.g., laterally outer portion 70) is free from attachment to any other components of the diaper at least along the segment of the side panels between the inner ends 62A, 64A of the front and back waist panels 62, 64, the leg cuff portions may also stretch in the lateral direction relative to and independent of the absorbent assembly 60, and the front and back waist panels without repositioning, expanding or otherwise reconfiguring the absorbent assembly.

It is contemplated that the lines of attachment (e.g., defined by adhesive 159) along which the lateral edge margins 88 of the absorbent assembly 60 are secured to the respective side panels 68 may be suitably disposed at a lateral position between the inboard and outboard edges 71, 73 of the side panels other than that illustrated in FIG. 3. It is also understood that the lines of attachment may even be disposed at the outboard edges 73 of the connecting members 68, or at the inboard edges 71 of the connecting members, without departing from the scope of this invention.

In the illustrated embodiment of FIG. 3, the absorbent assembly 60 is generally free from securement to the outer layer 48 of the diaper 20. It is understood, however, that in other embodiments a laterally central region of the absorbent assembly (e.g., laterally between the side edges of the absorbent structure 155) may be secured to the inner or body facing surface 50 of the outer layer 48 without departing from the scope of this invention.

Figure 3A:
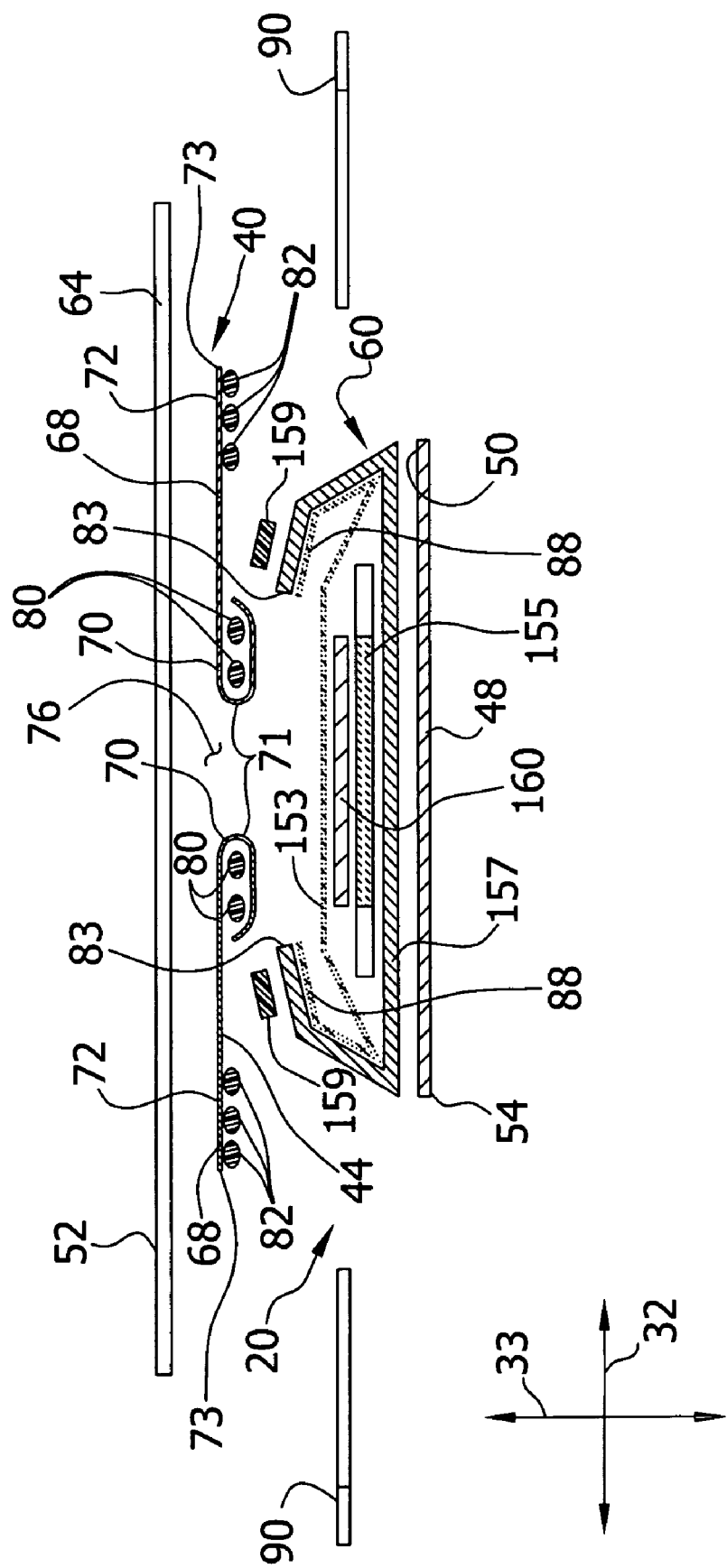
FIG. 3A is an exploded cross-section of an alternative embodiment of the invention.
Figure 4:
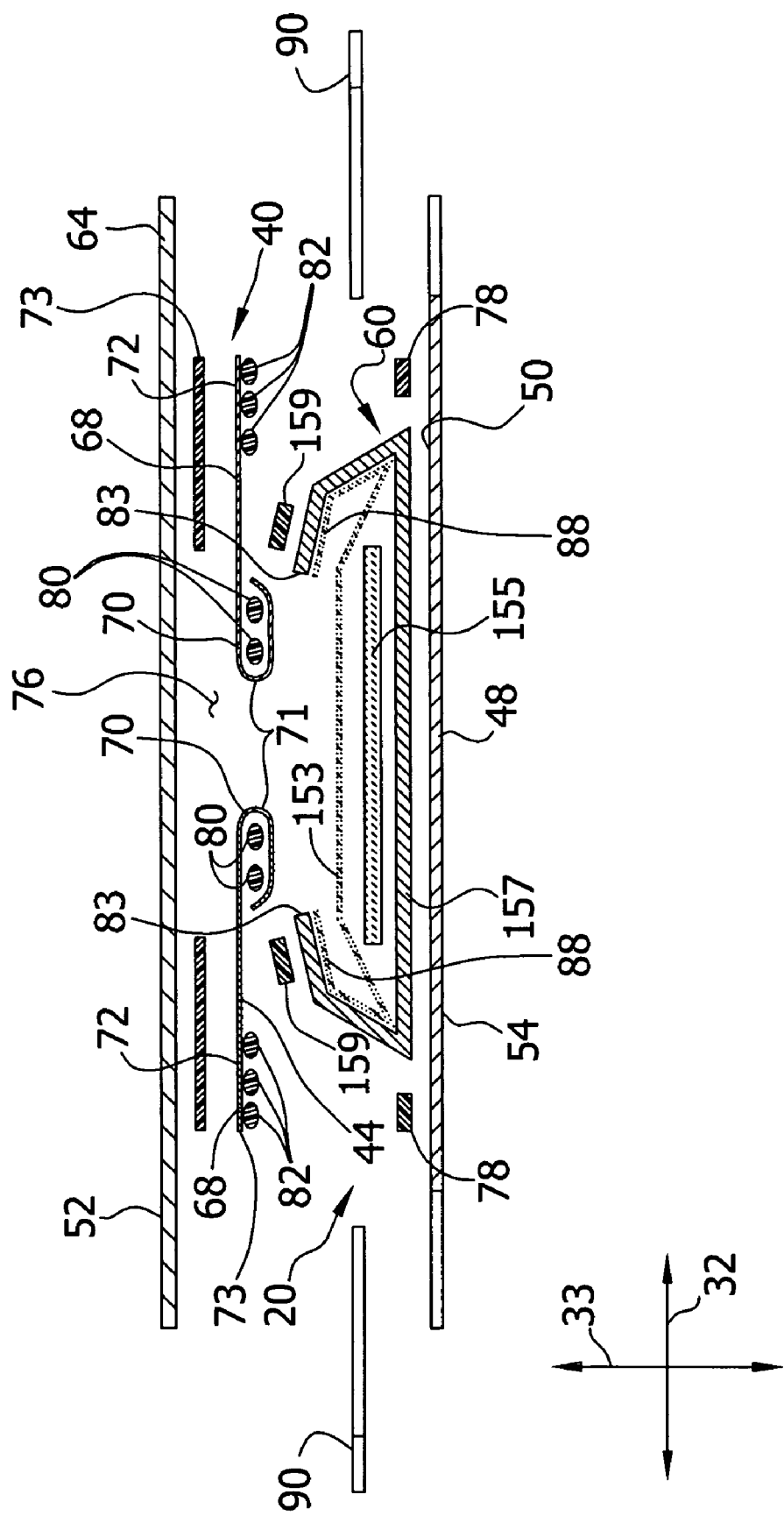
FIG. 4 is an exploded cross-section taken in the plane of line 4-4 of FIG. 1.

FIG. 3A illustrates an alternative embodiment of the diaper 20 (broadly, the garment) in which the outer layer 48 is substantially coextensive with the absorbent assembly 60 so that the outer layer is otherwise free from attachment to the side panels 68. In this embodiment the outboard edges 73 of the side panels 68 thus extend laterally beyond the lateral edges of the outer layer 48 particularly between the inner ends 62A, 64A of the waist panels 62, 64. Because the inboard and outboard edges 71, 73 of the side panels 68 of this embodiment are otherwise unsecured to the outer layer or other components of the diaper 20 at least along the segment of the side panels extending between the inner ends 62A, 62B of the waist panels 62, 64, the inboard and outboard edges of each side panel along such a segment are also positionable relative to and independent of the outer layer and the front and back waist panels. Where the side panels 68 are capable of lateral stretch, it is understood that the outer or leg cuff portion 72 of each side panel 68 is capable of lateral stretch independent of the outer layer 48 as well as the other components of the diaper 20.

It is understood that the outer layer 48 of FIG. 3A may be coextensive with the absorbent assembly in both the lateral direction 32 and longitudinal direction 30 of the article 20. It is alternatively contemplated that the outer layer 48 may be sized to extend laterally and/or longitudinally beyond the absorbent assembly without departing from the scope of this invention.

The outer layer 48 is suitably extensible in at least the lateral direction in accordance with the lateral stretchability of the side panels 68, particularly in the embodiment of FIG. 3 in which the outer portion 72 of each side panel is secured to the outer layer. The outer layer 48 is also suitably soft-feeling, compliant and "breathable" or vapor permeable material. As an example, an extensible outer layer 48 can be composed of a necked fabric, a creped fabric, a micro-pleated fabric, polymer films or the like, as well as combinations thereof. The fabrics may be woven or nonwoven materials, such as spunbond fabrics.

An example of a suitable extensible outer layer material is a 60% necked, polypropylene spunbond having a basis weight of about 1.2 osy. The necked spunbond material had the physical properties representatively shown in the stress-strain curve set forth in U.S. patent application Ser. No. 08/249,434 entitled EXPANDABLE COVER GARMENT by P. T. VanGompel et al. filed Feb. 12, 1999 and incorporated by reference herein. The properties of the spunbond material were determined with respect to a 2 inch wide sample having 3 inches of sample length spanning between an initial 3 inch separation of the holding jaws of a conventional set of tensile testing equipment.

Examples of suitable manufacturing techniques and suitable necked nonwoven fabric materials are described in U.S. Pat. No. 4,965,122 entitled REVERSIBLE NECKED MATERIAL AND PROCESS TO MAKE IT, by M. T. Morman which was issued Oct. 23, 1990. The entire disclosure of this document is incorporated herein by reference in a manner that is consistent herewith.

For the purposes of the present disclosure, the term "% necked" or "percent neckdown" refers to a ratio or percentage determined by measuring the difference between the pre-necked dimension and the necked dimension of a neckable material, and then dividing that difference by the pre-necked dimension of the neckable material. The percentage of necking (percent neck) can be determined in accordance with the description in the above-mentioned U.S. Pat. No. 4,965,122 entitled REVERSIBLE NECKED MATERIAL AND PROCESS TO MAKE IT, by M. T. Morman which was issued Oct. 23, 1990 and is incorporated by reference herein.

Alternatively, the outer layer 48 of the diaper 20 may be suitably constructed to be liquid impermeable. For example, in one embodiment the outer layer 48 may be comprised of a thin plastic film or other flexible liquid-impermeable material. A particularly suitable outer layer 48 material is a polyethylene film having a thickness of from about 0.012 millimeter (0.5 mil) to about 0.051 millimeter (2.0 mils). To present such an outer layer 48 with a more clothlike feeling, the outer layer 48 may further comprise a polyolefin film having a nonwoven web laminated to the outer surface thereof, such as a spunbond web of polyolefin fibers. For example, a stretch-thinned polypropylene film having a thickness of about 0.015 millimeter (0.6 mils) may have thermally laminated thereto a spunbond web of polypropylene fibers having a thickness of about 1.5 to 2.5 denier per filament, with the nonwoven web having a basis weight of about 17 grams per square meter (0.5 ounce per square yard). Methods of forming such clothlike outer layers are known to those skilled in the art. Alternatively, or additionally, the outer layer 48 may be formed of a woven or nonwoven fibrous web that has been totally or partially constructed or treated to impart a desired level of liquid impermeability to selected regions that are adjacent or proximate to the absorbent assembly 60.

In other embodiments, the outer layer 48 be suitably constructed to be permeable to water vapor and have a water vapor transmission rate (WVTR) of at least about 1000 g/m2/24 hours, more suitably at least about 1500 g/m2/24hours, even more suitably at least about 2000 g/m2/24 hours, and still more at least about 3000 g/m2/24 hours. Materials which have a water vapor transmission rate less than those above do not allow a sufficient amount of air exchange and undesirably result in increased levels of skin hydration. A suitable technique for determining the WVTR value of a material is the test procedure standardized by INDA (Association of the Nonwoven Fabrics Industry), number IST-70.4-99, which is incorporated by reference herein. The testing device which may be used for WVTR measurement is known as the Permatran-W Model 100K manufactured by Mocon/Modern Controls, Inc., with an office in Minneapolis, Minn.

In another suitable embodiment, the outer layer 48 may comprise a microporous film/nonwoven laminate material comprising a spunbond nonwoven material laminated to a microporous film. For example, the laminate may include a 0.6 osy (20.4 gsm) polypropylene spunbond material thermally attached to an 18.7 gsm stretched microporous film. The film may include from about 20 percent to about 75 percent by weight calcium carbonate particulates and the remainder primarily low density polyethylene. The film is then stretched which causes the polyethylene component to stretch while the particulates remain unstretched, thus causing voids to develop around the calcium carbonate particles in the film. The resulting laminate may define a water vapor transmission rate of from about 1000 to about 5000 g/m2/24 hours.

Additional examples of suitable breathable materials for the outer layer 48 are described in U.S. Pat. No. 5,879,341 issued Mar. 9, 1999 to Odorzynski et al. and entitled "ABSORBENT ARTICLE HAVING A BREATHABILITY GRADIENT"; U.S. Pat. No. 5,843,056 issued Dec. 1, 1988, to Good et al. and entitled ABSORBENT ARTICLE HAVING A COMPOSITE BREATHABLE OUTER COVER"; and U.S. Pat. No. 5,855,999 issued Jan. 5, 1999 to McCormack et al. and entitled "BREATHABLE, CLOTH-LIKE FILM/NONWOVEN COMPOSITE", the disclosures of which are herein incorporated by reference to the extent they are consistent herewith.

The outer layer 48 of the diaper 20 is preferably formed from a stretchable material so as to be extensible or even elastic to facilitate stretching of the outer layer along with the inner layer 40 of the diaper 20 as well as the side panels 68 (where the side panels are secured to the outer layer such as in the embodiment of FIG. 3). When the outer layer 48 is formed of a stretchable material, the outer layer is suitably capable of stretching in at least the lateral direction 32 and may additionally be stretchable in the longitudinal direction 30. It is contemplated that where the outer layer 48 is stretchable in both directions, it may be extensible in both directions, elastic in both directions, or extensible in one direction and elastic in the other direction.

Figure 5:
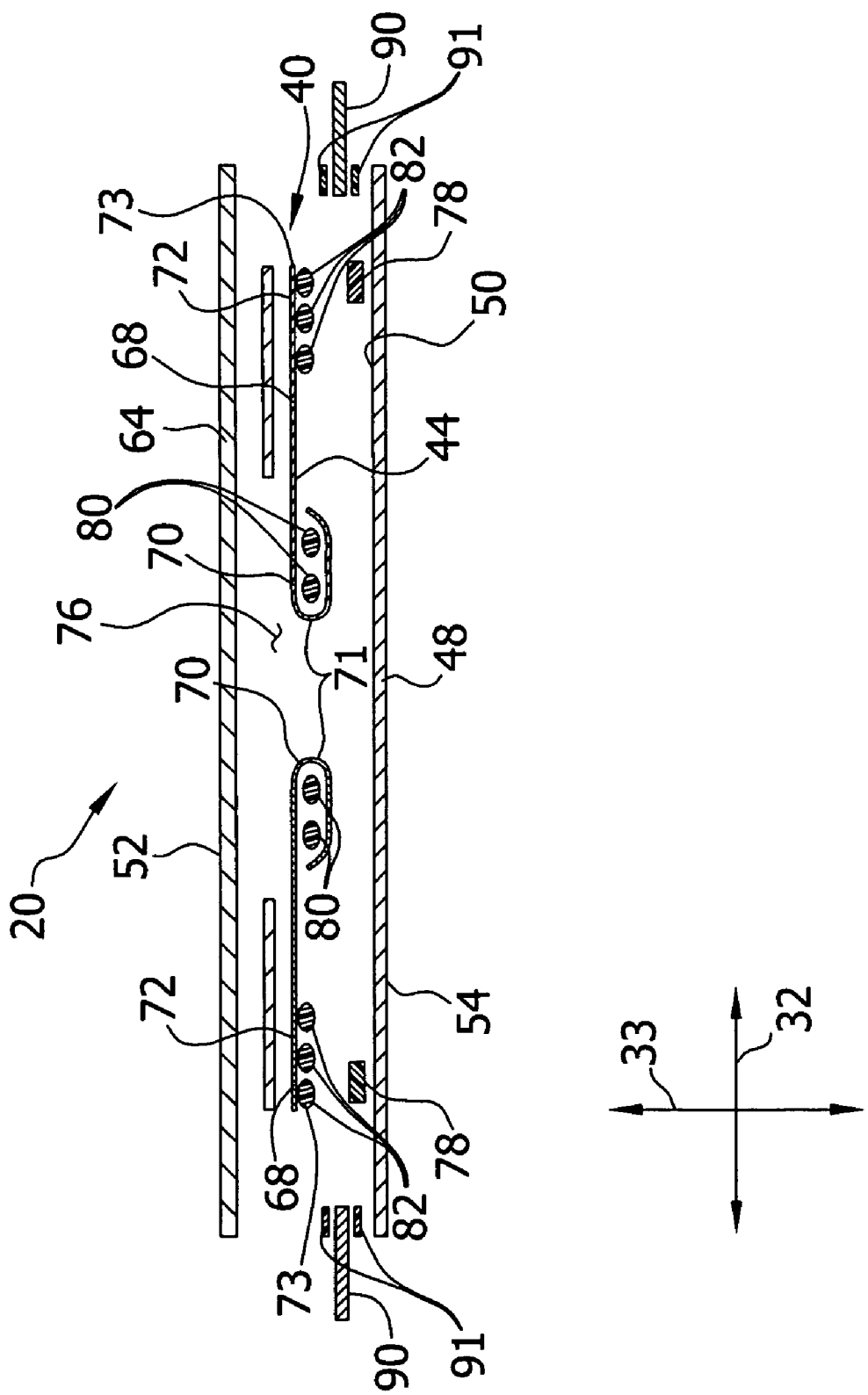
FIG. 5 is an exploded cross-section taken in the plane of line 5-5 of FIG. 1.

The front and back waist panels 62, 64 are suitably secured to the outer layer 48 at their respective coterminous edges by adhesive bonding, ultrasonic bonding, thermal bonding or other suitable securement technique. With reference to FIGS. 1 and 5, the diaper 20 may further comprise a pair of fastener tabs 90 employed to secure the diaper about the waist of a wearer. Suitable fastener tabs 90 include hook-and-loop type fasteners, adhesive tape fasteners, buttons, pins, snaps, mushroom-and-loop fasteners, and the like. In the illustrated embodiment the fastener tabs 90 are secured between the outer layer 48 and the back waist panel 64 at the side edges of the diaper 20 by suitable adhesive 91 (FIG. 5) and extend laterally outward therefrom. Cooperating fasteners 92 may be provided on the outer layer 48 in the front waist region 22 of the diaper. Alternatively, the outer layer 48 may be constructed of a material to which the fastener tabs 90 may be suitably fastened.

There are several suitable approaches for providing a disposable garment having a configuration similar to that of the diaper 20 of FIG. 1. For example, in one embodiment the elastic inner layer 40 can first be assembled by attaching the front and back waist panels 62, 64 to two continuous (and laterally spaced) webs of side panel 68 material. The C-folded absorbent assembly 60 is formed separately and then attached to the side panels 68 along the line of attachment (e.g., adhesive 159) to form the flap portions 70 and leg cuff portions 72 of the side panels. The outer layer 48 is then perimeter bonded to the front and back waist panels 62, 64. The front and back fasteners 90 may subsequently be added to the assembly, the leg openings die cut into the outer layer, and the individual diapers 20 sequentially cut.

Another suitable approach is to build the web of garments 20 from a continuous web of outer layer material. The C-folded absorbent assembly 60 is formed separately and a central region of the absorbent assembly is secured to the outer layer by securing the garment facing surface of the absorbent assembly to the body facing surface of the outer layer 48. The side panels 68 are constructed separately and then attached to the front and back waist panels 62, 64 to form the composite inner layer 40. The composite inner layer 40 is placed in registration with the C-folded absorbent assembly 60 and attached to the lateral edge margins 88 of the absorbent assembly by the adhesive layer 159. The inner layer 40 is then perimeter bonded to the outer layer 48. The front and back fasteners 90 are added and the leg openings are cut in the assembly. Finally, the web of assembled garments is sequentially cut into discrete garments.

When introducing elements of the present invention or the preferred aspect(s) thereof, the articles "a", "an", "the", and "said" are intended to mean that there are one or more of the elements. The terms "comprising," "including", and "having" are intended to be inclusive and mean that there may be additional elements other than the listed elements.

As various changes could be made in the above constructions without departing from the scope of the invention, it is intended that all matter contained in the above description or illustrated in the accompanying drawings shall be interpreted as illustrative and not in a limiting sense.

What is claimed is:

1. A disposable absorbent garment having a longitudinal direction, a lateral direction, a front waist region, a back waist region and a crotch region extending longitudinally between and interconnecting the front waist region and the back waist region, longitudinal ends and lateral side edges, the disposable absorbent garment comprising:

an inner layer having an interior surface for facing a wearer of the garment, and an exterior surface, the inner layer having a first end panel at least in part defining the front waist region of the garment, a second end panel separate from the first end panel and longitudinally spaced therefrom to at least in part define the back waist region of the garment, said first and second end panels each being stretchable in at least the lateral direction of the garment, and a pair of side panels formed separate from the first and second end panels and extending longitudinally between said first and second end panels in laterally spaced relationship with each other such that the end panels and side panels together define a central opening of the inner layer, the central opening being sized for allowing liquid, semi-liquid, and solid exudates released by the wearer to pass therethrough, said side panels each being secured to the first and second end panels and being extensible in at least the lateral direction of the garment;

an outer layer in opposed relationship with the inner layer; and an absorbent assembly disposed between the inner layer and the outer layer for receiving the liquid, semi-liquid, and solid exudates that passes through the inner layer at said central opening, the absorbent assembly being secured to the inner layer and being sized larger than the central opening of said inner layer for underlying substantially the entire opening.

2. The disposable absorbent garment set forth in claim 1 wherein the absorbent assembly has laterally spaced edge margins, said edge margins being secured respectively to the laterally spaced side panels of the inner layer to secure the absorbent assembly to the inner layer.

3. The disposable absorbent garment set forth in claim 1 wherein at least one longitudinal segment of each of the side panels is generally positionable relative to and independent of the absorbent assembly and end panels.

4. The disposable absorbent garment set forth in claim 3 wherein the at least one longitudinal segment is generally positionable relative to and independent of the outer layer.

5. The disposable absorbent garment set forth in claim 3 wherein the absorbent assembly has laterally spaced edge margins and each side panel has an inboard edge and an outboard edge, each edge margin of the absorbent assembly being secured to a respective side panel laterally intermediate the inboard edge and the outboard edge of the side panel along a longitudinal line of attachment, said line of attachment, the outboard edge of each side panel along at least a longitudinal segment thereof being positionable about said line of attachment relative to and independent of the absorbent assembly, outer layer and end panels.

6. The disposable absorbent garment set forth in claim 5 wherein the portion of each side panel laterally between the outboard edge of the side panel and the line of attachment defines a leg cuff portion of the side panel, said leg cuff portion being stretchable in the lateral direction of the garment independent of the absorbent assembly and end panels at least along said longitudinal segment of the side panel.

7. The disposable absorbent garment set forth in claim 6 wherein the leg cuff portion of each side panel is also elastic in the longitudinal direction of the garment.

8. The disposable absorbent garment set forth in claim 6 wherein the portion of each side panel laterally between the inboard edge of the side panel and the line of attachment defines a containment flap portion of the side panel, said containment flap portion being elastic in the longitudinal direction of the garment.

9. The disposable absorbent garment set forth in claim 1 wherein garment further has a z-direction normal to the longitudinal and lateral directions thereof, the absorbent assembly being expandable during wear in at least the z-direction of the garment.

10. The disposable absorbent garment set forth in claim 1 wherein the first and second end panels are substantially liquid impermeable.

11. The disposable absorbent garment set forth in claim 1 wherein the side panels are substantially liquid impermeable.

12. The disposable absorbent garment set forth in claim 1 wherein the outer layer of the garment is stretchable in at least the lateral direction of the garment.

13. The disposable absorbent garment set forth in claim 1 wherein each of the side panels has longitudinally opposite end margins respectively secured to the first and second end panels.

14. A disposable absorbent garment having a longitudinal direction, a lateral direction, a front waist region, a back waist region and a crotch region extending longitudinally between and interconnecting the front waist region and the back waist region, longitudinal ends and lateral side edges, the disposable absorbent garment comprising:

an inner layer having an interior surface for facing a wearer of the garment, and an exterior surface, the inner layer having a first end panel at least in part defining the front waist region of the garment, a second end panel separate from the first end panel and longitudinally spaced from the first end panel to at least in part define the back waist region of the garment, said first and second end panels each being stretchable in at least the lateral direction of the garment, and a pair of laterally spaced side panels extending longitudinally between and secured to said first and second end panels to at least in part define the crotch region of the garment, said side panels being extensible in at least the lateral direction of the garment, said end panels and said side panels together defining a central opening of the inner layer, the central opening being sized for allowing liquid, semi-liquid, and solid exudates released by the wearer to pass therethrough;

an outer layer in opposed relationship with the inner layer; and an absorbent assembly disposed between the inner layer and the outer layer for receiving the liquid, semi-liquid, and solid exudates that passes through the inner layer, the absorbent assembly having laterally spaced edge margins, each edge margin of the absorbent assembly being secured to a respective one of the side panels along a respective longitudinal line of attachment whereby at least a longitudinal segment of each side panel is positionable about the line of attachment and relative to and independent of the absorbent assembly and end panels, each side panel further comprising a longitudinally extending elastic member extending along at least said longitudinal segment of the side panel, said elastic member being in laterally spaced relationship with the longitudinal line of attachment between the absorbent assembly edge margin and the respective side panel to generally urge said longitudinal segment of the side panel against the wearer.

15. The disposable absorbent garment set forth in claim 14 wherein said longitudinal segment is extensible in the longitudinal direction of the article relative to and independent of the absorbent assembly.

16. The disposable absorbent garment set forth in claim 14 wherein the longitudinally extending elastic member is disposed laterally inboard of the longitudinal line of attachment.

17. The disposable absorbent garment set forth in claim 14 wherein the longitudinally extending elastic member is disposed laterally outboard of the longitudinal line of attachment.

18. The disposable absorbent garment set forth in claim 16 wherein the elastic member is a first elastic member, each side panel further comprising a second longitudinally extending elastic member secured thereto at least along said longitudinal segment of the side panel, said second elastic member being disposed laterally outboard of the longitudinal line of attachment.

19. The disposable absorbent garment set forth in claim 14 wherein the longitudinal segment of each side panel is positionable relative to and independent of the outer layer.

20. A disposable absorbent garment for personal wear, the garment having a longitudinal direction and a lateral direction, said disposable absorbent garment comprising:
an inner layer having an interior surface for facing a wearer of the garment, and an exterior surface, the inner layer comprising a first end panel and a second end panel spaced longitudinally from the first end panel, said first and second end panels each being stretchable in at least the lateral direction of the garment, and a pair of laterally spaced side panels extending longitudinally between and secured to said first and second end panels, said side panels and end panels together defining a central opening of the inner layer, the central opening being sized for allowing liquid, semi-liquid, and solid exudates released by the wearer to pass therethrough, at least a portion of each of said side panels defining leg cuffs of the garment adapted for contact with the wearer's legs, said leg cuff portion of each side panel being extensible in at least the lateral direction of the garment, the leg cuff portion of each side panel comprising at least one longitudinally extending elastic member for urging the leg cuff generally against the garment wearer's skin;
an outer layer in opposed relationship with the inner layer; and
an absorbent assembly disposed between the inner layer and the outer layer for receiving the liquid, semi-liquid, and solid exudates that passes through the inner layer, the absorbent assembly having laterally spaced edge margins, each edge margin of the absorbent assembly being secured to a respective one of the side panels along a respective longitudinal line of attachment disposed laterally inward of the leg cuff portion of the side panel such that the at least one elastic member of the leg cuff is disposed laterally outboard of the longitudinal line of the attachment, the leg cuff portion of each side panel being free from securement to the absorbent assembly and the end panels of the garment at least along a longitudinal segment of each leg cuff portion so that the leg cuff portion along said segment is stretchable in the lateral direction of the garment independent of the absorbent assembly and the end panels.

21. The disposable absorbent garment set forth in claim 20 wherein the side panels are formed separate from the outer layer and the first and second end panels of the inner layer.

22. The disposable absorbent garment set forth in claim 20 wherein the longitudinal segment of each leg cuff portion is free from securement to the outer layer so that the leg cuff portion along the segment is stretchable in the lateral direction of the garment independent of the outer layer.

23. The disposable absorbent garment set forth in claim 20 wherein the leg cuff is positionable relative to the absorbent assembly.

24. The disposable absorbent garment set forth in claim 23 wherein the leg cuff is positionable relative to the outer layer.

25. A disposable absorbent garment having a longitudinal direction, a lateral direction, a front waist region, a back waist region and a crotch region extending longitudinally between and interconnecting the front waist region and the back waist region, longitudinal ends and lateral side edges, the disposable absorbent garment comprising:
an inner layer having an interior surface for facing a wearer of the garment, and an exterior surface, the inner layer having a first end panel at least in part defining the front waist region of the garment, a second end panel separate from the first end panel and longitudinally spaced from the first end panel to at least in part define the back waist region of the garment, said first and second end panels each being stretchable in at least the lateral direction of the garment, and a pair of laterally spaced side panels formed separate from the first and second end panels and extending longitudinally between and secured to said first and second end panels to at least in part define the crotch region of the garment, said side panels each having an inboard edge and an outboard edge and being elastic in at least the longitudinal direction of the garment, said end panels and said side panels together defining a central opening of the inner layer, the central opening being sized for allowing liquid, semi-liquid, and solid exudates released by the wearer to pass therethrough;
an outer layer in opposed relationship with the inner layer; and
an absorbent assembly disposed between the inner layer and the outer layer for receiving the liquid, semi-liquid, and solid exudates that passes through the inner layer, the absorbent assembly having laterally spaced edge margins, each edge margin of the absorbent assembly being secured to a respective one of the side panels along a respective longitudinal line of attachment disposed laterally between the inboard and outboard edges of the side panel, the inboard and outboard edges of each side panel being positionable about the respective line of attachment relative to and independent of the absorbent assembly and the end panels along at least a longitudinal segment of each side panel.

26. A disposable absorbent garment having a longitudinal direction, a lateral direction, a front waist region, a back waist region and a crotch region extending longitudinally between and interconnecting the front waist region and the back waist region, longitudinal ends and lateral side edges, the disposable absorbent garment comprising:
an inner layer having an interior surface for facing a wearer of the garment, and an exterior surface, the inner layer having a first end panel at least in part defining the front waist region of the garment, a second end panel separate from the first end panel and longitudinally spaced therefrom to at least in part define the back waist region of the garment, said first and second end panels each being stretchable in at least the lateral direction of the garment, and a pair of side panels formed separate from the first and second end panels and extending longitudinally between said first and second end panels in laterally spaced relationship with each other such that the end panels and side panels together define a single, central opening of the inner layer, the central opening being sized for allowing solid body waste released by the wearer to pass therethrough, said side panels each being secured to the first and second end panels and being extensible in at least the lateral direction of the garment;

an outer layer in opposed relationship with the inner layer; and an absorbent assembly disposed between the inner layer and the outer layer for receiving the solid body waste that passes through the inner layer at said central opening, the absorbent assembly being secured to the inner layer and being sized larger than the central opening of said inner layer for underlying substantially the entire opening.

* * * * *